US007704709B2

(12) United States Patent
Kwon et al.

(10) Patent No.: US 7,704,709 B2
(45) Date of Patent: Apr. 27, 2010

(54) MODIFIED HUMAN GRANULOCYTE-COLONY STIMULATING FACTOR AND PROCESS FOR PRODUCING SAME

(75) Inventors: Se-Chang Kwon, Seoul (KR); Sung-Youb Jung, Seoul (KR); Sung-Min Bae, Seoul (KR); Gwan-Sun Lee, Seoul (KR)

(73) Assignee: Hanmi Pharm. Co., Ltd, Hwaseong-Gun (KR)

( * ) Notice: Subject to any disclaimer, the term of this patent is extended or adjusted under 35 U.S.C. 154(b) by 7 days.

(21) Appl. No.: 11/975,541

(22) Filed: Oct. 19, 2007

(65) Prior Publication Data

US 2008/0064066 A1 Mar. 13, 2008

Related U.S. Application Data

(63) Continuation of application No. 10/031,123, filed on Jan. 9, 2002, now abandoned, which is a continuation of application No. PCT/KR00/00733, filed on Jul. 7, 2000.

(30) Foreign Application Priority Data

Jul. 8, 1999 (KR) .................................. 99-27418

(51) Int. Cl.
*C07K 14/00* (2006.01)
*C07K 14/435* (2006.01)
*C07K 14/46* (2006.01)
*C07K 14/47* (2006.01)
*C07K 14/475* (2006.01)
*C07K 14/52* (2006.01)
*C07K 14/53* (2006.01)
*C07K 14/535* (2006.01)
*C12N 15/09* (2006.01)
*C12N 15/11* (2006.01)
*C12N 15/12* (2006.01)
*C12N 15/19* (2006.01)
*C12N 15/27* (2006.01)
*C12N 15/63* (2006.01)
*C12N 15/70* (2006.01)
*C12N 15/72* (2006.01)

(52) U.S. Cl. ..................... 435/69.1; 435/69.4; 435/69.5; 435/69.8; 435/69.9; 435/325; 435/252.3; 435/254.11; 435/320.1; 530/350; 530/351; 536/23.1; 536/23.5; 536/23.51; 536/24.1

(58) Field of Classification Search ........................ None
See application file for complete search history.

(56) References Cited

U.S. PATENT DOCUMENTS

| 4,810,643 | A | 3/1989 | Souza |
| 5,362,853 | A | 11/1994 | Kuga et al. |
| 5,416,195 | A | 5/1995 | Camble et al. |
| 5,427,927 | A | 6/1995 | Meyer et al. |
| 5,451,660 | A | 9/1995 | Builder et al. |
| 5,710,027 | A | 1/1998 | Hauptmann et al. |
| 5,795,968 | A | 8/1998 | Kuga et al. |
| 6,100,070 | A | 8/2000 | Zurfluh et al. |
| 6,476,198 | B1 | 11/2002 | Kang |
| 6,498,233 | B1 | 12/2002 | Wels et al. |
| 2004/0018586 | A1 | 1/2004 | Rosendahl et al. |

FOREIGN PATENT DOCUMENTS

| EP | 0 256 843 A1 | 2/1988 |
| JP | 1990-104598 | 4/1990 |
| WO | WO 96/13599 A1 | 5/1996 |
| WO | WO 97/01580 A1 | 1/1997 |
| WO | WO 00/15661 A1 | 3/2000 |

OTHER PUBLICATIONS

Biotechnol Prog 1995, 11(2):171-1.
J Fla Med Assoc, 1994, 81 (7):467-9.
Plasmid 1997:38(3):158-73.
Gene 1996, 173 (2): 271-4.
Biochem J 1994, 15;298 Pt 3:719-25.
DeFrees, S., et al., "GlycoPEGylation of recombinant therapeutic proteins produced in *Escherichia coli*," Glycobiology, vol. 16, No. 9, pp. 833-843, 2006.
Souza, L., et al., "Recombinant Human Granulocyte Colony-Stimulating Factor: Effects on Normal and Leukemic Myeloid Cells," Science, vol. 232, pp. 61-65, Apr. 4, 1986.
Rinderknecht, E., et al., "The Amino Acid Sequence of Human Insulin-like Growth Factor I and its Structural Homology with Proinsulin," J. Bio. Chem., vol. 253, No. 8, pp. 2769-2776, Apr. 25, 1978.
Arakawa, t., et al., "Cysteine 17 of Recombinant Human Granulocyte-Colony Stimulating Factor is Partially Solvent-Exposed," J. Protein Chemistry, XP-001056383, vol. 12, No. 5, 1993.
Kuwabara, T., et al., "Highly Sensitive Enzyme-Linked Immunosorbent Assay for Marograstim (KW-2228) a Mutant of Human Granulocyte Colony Stimulating Factor," J. Pharmacobio-Dyn., XP-001106498, vol. 15, pp. 121-129 (1992).
Devlin, P.E., "Alteration of amino-terminal codons of human granulocyte-colony-Colony stimulating factor increases expression levels and allows efficient processing by methionine aminopeptidase in *Escherichia coli*," Dept. Molecular Bio. And Protein Chem., Cetus Corporation, Emeryville, CA 94608, XP-001024074, pp. 13-22.
"DNAK/DNAJ Supplementation Improves the Periplasmic Production of Human Granulocyte-Colony Stimulating Factor in *Escherichia coli*," Biochem. And Biophy. Research Comm, vol. 210, No. 2, pp. 524-529, 1995.
"Overproduction of Human Granulocyte-Colony Stimulating Factor Fused to the Pel B Signal Peptide in *Escherichia coli*," J. of Fermentation and Bioeng., vol. 85, No. 4, pp. 443-446, 1998.

(Continued)

*Primary Examiner*—Elizabeth C. Kemmerer
(74) *Attorney, Agent, or Firm*—Sughrue Mion, PLLC

(57) ABSTRACT

A modified human granulocyte-colony stimulating factor (hG-CSF) is produced by culturing a microorganism transformed with an expression vector comprising a gene encoding a modified hG-CSF to produce and secrete the modified hG-CSF to periplasm, said modified hG-CSF being obtained by replacing at least one of the 1st, 2nd, 3rd and 17th amino acids of wild-type hG-CSF (SEQ ID NO: 2) with other amino acid.

28 Claims, 11 Drawing Sheets

OTHER PUBLICATIONS

"Strategies for Achieving High-Level Expression of Genes in *Escherichia coli*," Microbiological Reviews, vol. 60, No. 3, pp. 512-538, Sep. 1996.

European Patent Office Opposition against European Patent No. 1 194 575 dated Sep. 15, 2008.

Search result from query of NBCI online sequence database using SEQ ID No. 42 of opposed patent http://www.ncbi.nlm.nih.gov/sites/gquery?term=mkkllfaiplvvpfyshs.

Watson, Nucleic acids research, vol. 12, No. 13, 1984, pp. 5145-5164.

Vassileva-Atanassova, Anelia, et al., "N-terminal methionine in recombinant proteins expressed in two different *Escherichia coli* strains," J. of Biotechnology, vol. 69, Mar. 26, 1999, pp. 63-67.

Fig. 1

```
T   P   L   G   P   A   S   S   L   P   Q   S   F   L   L   K
aca ccc ctg ggc cct gcc agc tcc ctg ccc cag agc ttc ctg ctc aag C   L   E   Q   V   R   K   I   Q   G   D   G   A   A   L   Q
tgc tta gag caa gtg agg aag atc cag ggc gat ggc gca gcg ctc cag E   K   L   C   A   T   Y   K   L   C   H   P   E   E   L   V
gag aag ctg tgt gcc acc tac aag ctg tgc cac ccc gag gag ctg gtg L   L   G   H   S   L   G   I   P   W   A   P   L   S   S   C
ctg ctc gga cac tct ctg ggc atc ccc tgg gct ccc ctg agc tcc tgc P   S   Q   A   L   Q   L   A   G   C   L   S   Q   L   H   S
ccc agc cag gcc ctg cag ctg gca ggc tgc ttg agc caa ctc cat agc G   L   F   L   Y   Q   G   L   L   Q   A   L   E   G   I   S
ggc ctt ttc ctc tac cag ggg ctc ctg cag gcc ctg gaa ggg ata tcc P   E   L   G   P   T   L   D   T   L   Q   L   D   V   A   D
ccc gag ttg ggt ccc acc ttg gac aca ctg cag ctg gac gtc gcc gac F   A   T   T   I   W   Q   Q   M   E   E   L   G   M   A   P
ttt gcc acc acc atc tgg cag cag atg gaa gaa ctg gga atg gcc cct A   L   Q   P   T   Q   G   A   M   P   A   F   A   S   A   F
gcc ctg cag ccc acc cag ggt gcc atg ccg gcc ttc gcc tct gct ttc Q   R   R   A   G   G   V   L   V   A   S   H   L   Q   S   F
cag cgc cgg gca gga ggg gtc ctg gtt gct agc cat ctg cag agc ttc L   E   V   S   Y   R   V   L   R   H   L   A   Q   P
ctg gag gtg tcg tac cgc gtt cta cgc cac ctt gcg cag ccc
```

SEQUENCE LISTING

<160> NUMBER OF SEQ ID NOS: 71

<210> SEQ ID NO 1
<211> LENGTH: 522
<212> TYPE: DNA
<213> ORGANISM: Homo sapiens
<220> FEATURE:
<221> NAME/KEY: CDS
<222> LOCATION: (1)..(522)

<400> SEQUENCE: 1

```
aca ccc ctg ggc cct gcc agc tcc ctg ccc cag agc ttc ctg ctc aag      48
Thr Pro Leu Gly Pro Ala Ser Ser Leu Pro Gln Ser Phe Leu Leu Lys
 1               5                  10                  15 tgc tta gag caa gtg agg aag atc cag ggc gat ggc gca gcg ctc cag      96
Cys Leu Glu Gln Val Arg Lys Ile Gln Gly Asp Gly Ala Ala Leu Gln
             20                  25                  30 gag aag ctg tgt gcc acc tac aag ctg tgc cac ccc gag gag ctg gtg     144
Glu Lys Leu Cys Ala Thr Tyr Lys Leu Cys His Pro Glu Glu Leu Val
         35                  40                  45 ctg ctc gga cac tct ctg ggc atc ccc tgg gct ccc ctg agc tcc tgc     192
Leu Leu Gly His Ser Leu Gly Ile Pro Trp Ala Pro Leu Ser Ser Cys
     50                  55                  60 ccc agc cag gcc ctg cag ctg gca ggc tgc ttg agc caa ctc cat agc     240
Pro Ser Gln Ala Leu Gln Leu Ala Gly Cys Leu Ser Gln Leu His Ser
 65                  70                  75                  80 ggc ctt ttc ctc tac cag ggg ctc ctg cag gcc ctg gaa ggg ata tcc     288
Gly Leu Phe Leu Tyr Gln Gly Leu Leu Gln Ala Leu Glu Gly Ile Ser
                 85                  90                  95 ccc gag ttg ggt ccc acc ttg gac aca ctg cag ctg gac gtc gcc gac     336
Pro Glu Leu Gly Pro Thr Leu Asp Thr Leu Gln Leu Asp Val Ala Asp
            100                 105                 110 ttt gcc acc acc atc tgg cag cag atg gaa gaa ctg gga atg gcc cct     384
Phe Ala Thr Thr Ile Trp Gln Gln Met Glu Glu Leu Gly Met Ala Pro
        115                 120                 125 gcc ctg cag ccc acc cag ggt gcc atg ccg gcc ttc gcc tct gct ttc     432
Ala Leu Gln Pro Thr Gln Gly Ala Met Pro Ala Phe Ala Ser Ala Phe
    130                 135                 140 cag cgc cgg gca gga ggg gtc ctg gtt gct agc cat ctg cag agc ttc     480
Gln Arg Arg Ala Gly Gly Val Leu Val Ala Ser His Leu Gln Ser Phe
145                 150                 155                 160 ctg gag gtg tcg tac cgc gtt cta cgc cac ctt gcg cag ccc               522
Leu Glu Val Ser Tyr Arg Val Leu Arg His Leu Ala Gln Pro
                165                 170
```

<210> SEQ ID NO 2
<211> LENGTH: 174
<212> TYPE: PRT
<213> ORGANISM: Homo sapiens

<400> SEQUENCE: 2

```
Thr Pro Leu Gly Pro Ala Ser Ser Leu Pro Gln Ser Phe Leu Leu Lys
 1               5                  10                  15

Cys Leu Glu Gln Val Arg Lys Ile Gln Gly Asp Gly Ala Ala Leu Gln
             20                  25                  30

Glu Lys Leu Cys Ala Thr Tyr Lys Leu Cys His Pro Glu Glu Leu Val
         35                  40                  45

Leu Leu Gly His Ser Leu Gly Ile Pro Trp Ala Pro Leu Ser Ser Cys
     50                  55                  60
```

```
Pro Ser Gln Ala Leu Gln Leu Ala Gly Cys Leu Ser Gln Leu His Ser
 65                  70                  75                  80

Gly Leu Phe Leu Tyr Gln Gly Leu Leu Gln Ala Leu Glu Gly Ile Ser
                 85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Pro
        115                 120                 125

Ala Leu Gln Pro Thr Gln Gly Ala Met Pro Ala Phe Ala Ser Ala Phe
    130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro
                165                 170

<210> SEQ ID NO 3
<211> LENGTH: 32
<212> TYPE: DNA
<213> ORGANISM: Artificial Sequence
<220> FEATURE:
<223> OTHER INFORMATION: Oligonucleotide primer for the N-terminal of
      hG-CSF

<400> SEQUENCE: 3
cgccgccata tgacacccct gggccctgcc ag                                   32

<210> SEQ ID NO 4
<211> LENGTH: 36
<212> TYPE: DNA
<213> ORGANISM: Artificial Sequence
<220> FEATURE:
<223> OTHER INFORMATION: Oligonucleotide primer for the C-terminal of
      hG-CSF

<400> SEQUENCE: 4
accgaattcg gatcctcagg gctgcgcaag gtggcg                               36

<210> SEQ ID NO 5
<211> LENGTH: 72
<212> TYPE: DNA
<213> ORGANISM: Artificial Sequence
<220> FEATURE:
<223> OTHER INFORMATION: Oligonucleotide for preparing E. coli
      enterotoxin II signal peptide

<400> SEQUENCE: 5
tcatgaaaaa gaatatcgca tttcttcttg catctatgtt cgttttttct attgctacaa    60
atgcctacgc gt                                                        72

<210> SEQ ID NO 6
<211> LENGTH: 72
<212> TYPE: DNA
<213> ORGANISM: Artificial Sequence
<220> FEATURE:
<223> OTHER INFORMATION: Oligonucleotide for preparing E. coli
      enterotoxin II signal peptide

<400> SEQUENCE: 6
acgcgtaggc atttgtagca atagaaaaaa cgaacataga tgcaagaaga aatgcgatat    60 tcttttttcat ga                                                       72

<210> SEQ ID NO 7
```

```
<211> LENGTH: 39
<212> TYPE: DNA
<213> ORGANISM: Artificial Sequence
<220> FEATURE:
<223> OTHER INFORMATION: Oligonucleotide primer coding for the
      N-terminal of [Ser1]hG-CSF

<400> SEQUENCE: 7
acaaatgcct acgcgtctcc cctgggccct gccagctcc                          39

<210> SEQ ID NO 8
<211> LENGTH: 42
<212> TYPE: DNA
<213> ORGANISM: Artificial Sequence
<220> FEATURE:
<223> OTHER INFORMATION: Oligonucleotide primer coding for the
      C-terminal of [Ser1]hG-CSF

<400> SEQUENCE: 8
accgaattcg gatcctcagg gctgcgcaag gtggcgtaga ac                      42

<210> SEQ ID NO 9
<211> LENGTH: 65
<212> TYPE: DNA
<213> ORGANISM: Artificial Sequence
<220> FEATURE:
<223> OTHER INFORMATION: Oligonucleotide primer coding for E.coli
      enterotoxin II Shine-Dalgarno sequence

<400> SEQUENCE: 9
cggtttccct ctagaggttg aggtgtttta tgaaaaagaa tatcgcattt cttcttgcat   60
ctatg                                                               65

<210> SEQ ID NO 10
<211> LENGTH: 45
<212> TYPE: DNA
<213> ORGANISM: Artificial Sequence
<220> FEATURE:
<223> OTHER INFORMATION: Oligonucleotide containing BamHI restriction
      site

<400> SEQUENCE: 10
accgaattcg gatcctcagg gctgcgcaag gtggcgtaga acgcg                   45

<210> SEQ ID NO 11
<211> LENGTH: 10
<212> TYPE: PRT
<213> ORGANISM: Artificial Sequence
<220> FEATURE:
<223> OTHER INFORMATION: Last five amino acids of E. coli enterotoxin II
      signal peptide plus the 1st to the 5th amino acids of hG-CSF

<400> SEQUENCE: 11

Thr Asn Ala Tyr Ala Thr Pro Leu Gly Pro
  1               5                  10

<210> SEQ ID NO 12
<211> LENGTH: 30
<212> TYPE: DNA
<213> ORGANISM: Artificial Sequence
<220> FEATURE:
<223> OTHER INFORMATION: Oligonucleotide for preparing [Thr1]hG-CSF

<400> SEQUENCE: 12
acaaatgcct acgcgacacc cctgggccct                                    30
```

```
<210> SEQ ID NO 13
<211> LENGTH: 30
<212> TYPE: DNA
<213> ORGANISM: Artificial Sequence
<220> FEATURE:
<223> OTHER INFORMATION: Antisense of SEQ ID NO: 12

<400> SEQUENCE: 13
agggcccagg ggtgtcgcgt aggcatttgt                                        30

<210> SEQ ID NO 14
<211> LENGTH: 8
<212> TYPE: PRT
<213> ORGANISM: Artificial Sequence
<220> FEATURE:
<223> OTHER INFORMATION: N-terminal sequence of E. coli enterotoxin II
      signal peptide having threonine as the 4th amino acid

<400> SEQUENCE: 14

Met Lys Lys Thr Ile Ala Phe Leu
 1               5

<210> SEQ ID NO 15
<211> LENGTH: 33
<212> TYPE: DNA
<213> ORGANISM: Artificial Sequence
<220> FEATURE:
<223> OTHER INFORMATION: Oligonucleotide for substituting the 4th amino
      acid of E. coli enterotoxin II signal peptide with threonine

<400> SEQUENCE: 15
ggtgttttat gaaaaagaca atcgcatttc ttc                                    33

<210> SEQ ID NO 16
<211> LENGTH: 33
<212> TYPE: DNA
<213> ORGANISM: Artificial Sequence
<220> FEATURE:
<223> OTHER INFORMATION: Antisense of SEQ ID NO: 15

<400> SEQUENCE: 16
gaagaaatgc gattgtcttt ttcataaaac acc                                    33

<210> SEQ ID NO 17
<211> LENGTH: 8
<212> TYPE: PRT
<213> ORGANISM: Artificial Sequence
<220> FEATURE:
<223> OTHER INFORMATION: C-terminal sequence of E. coli enterotoxin II
      signal peptide having glutamine as the 22nd amino acid

<400> SEQUENCE: 17

Asn Ala Gln Ala Thr Pro Leu Gly
 1               5

<210> SEQ ID NO 18
<211> LENGTH: 26
<212> TYPE: DNA
<213> ORGANISM: Artificial Sequence
<220> FEATURE:
<223> OTHER INFORMATION: Oligonucleotide for substituting the 22nd amino
      acid of E. coli enterotoxin II signal peptide with glutamine

<400> SEQUENCE: 18
caaatgccca agcgacaccc ctgggc                                            26

<210> SEQ ID NO 19
```

-continued

```
<211> LENGTH: 26
<212> TYPE: DNA
<213> ORGANISM: Artificial Sequence
<220> FEATURE:
<223> OTHER INFORMATION: Antisense of SEQ ID NO: 18

<400> SEQUENCE: 19
gcccaggggt gtcgcttggg catttg                                          26

<210> SEQ ID NO 20
<211> LENGTH: 24
<212> TYPE: DNA
<213> ORGANISM: Artificial Sequence
<220> FEATURE:
<223> OTHER INFORMATION: Oligonucleotide for modifying E. coli
      enterotoxin II Shine-Dalgarno sequence

<400> SEQUENCE: 20
tctagaggtt gaggtgtttt atga                                            24

<210> SEQ ID NO 21
<211> LENGTH: 24
<212> TYPE: DNA
<213> ORGANISM: Artificial Sequence
<220> FEATURE:
<223> OTHER INFORMATION: Antisense of SEQ ID NO: 20

<400> SEQUENCE: 21
tcataaaaca cctcaacctc taga                                            24

<210> SEQ ID NO 22
<211> LENGTH: 66
<212> TYPE: DNA
<213> ORGANISM: Artificial Sequence
<220> FEATURE:
<223> OTHER INFORMATION: S1 oligomer having E. coli-preferred nucleotide
      sequence coding for the 6th to 26th amino acids of [Ser17]hG-CSF

<400> SEQUENCE: 22
cagcctcttc tcttccacaa tctttccttc ttaagtctct tgaacaagtt agaaagatcc     60
aaggcg                                                                66

<210> SEQ ID NO 23
<211> LENGTH: 66
<212> TYPE: DNA
<213> ORGANISM: Artificial Sequence
<220> FEATURE:
<223> OTHER INFORMATION: Antisense of SEQ ID NO: 22 (AS1 oligomer)

<400> SEQUENCE: 23
ccgggtcgga gaagagaagg tgttagaaag gaagaattca gagaacttgt tcaatctttc     60
taggtt                                                                66

<210> SEQ ID NO 24
<211> LENGTH: 21
<212> TYPE: PRT
<213> ORGANISM: Escherichia coli
<220> FEATURE:
<221> NAME/KEY: SIGNAL
<222> LOCATION: (1)..(21)
<223> OTHER INFORMATION: E. coli OmpA signal peptide

<400> SEQUENCE: 24

Met Lys Lys Thr Ala Ile Ala Ile Ala Val Ala Leu Ala Gly Phe Ala
  1               5                  10                  15
```

Thr Val Ala Gln Ala
          20

<210> SEQ ID NO 25
<211> LENGTH: 18
<212> TYPE: DNA
<213> ORGANISM: Artificial Sequence
<220> FEATURE:
<223> OTHER INFORMATION: Oligonucleotide containing Hind III recognition
      site

<400> SEQUENCE: 25
gttgcgcaag cttctcga                                                 18

<210> SEQ ID NO 26
<211> LENGTH: 18
<212> TYPE: DNA
<213> ORGANISM: Artificial Sequence
<220> FEATURE:
<223> OTHER INFORMATION: Antisense of SEQ ID NO: 25

<400> SEQUENCE: 26
tcgagaagct tgcgcaac                                                 18

<210> SEQ ID NO 27
<211> LENGTH: 39
<212> TYPE: DNA
<213> ORGANISM: Artificial Sequence
<220> FEATURE:
<223> OTHER INFORMATION: Oligonucleotide for the N-terminal of
      [Ser1]hG-CSF

<400> SEQUENCE: 27
gttgcgcaag cttctccct gggccctgcc agctccctg                           39

<210> SEQ ID NO 28
<211> LENGTH: 39
<212> TYPE: DNA
<213> ORGANISM: Artificial Sequence
<220> FEATURE:
<223> OTHER INFORMATION: Oligonucleotide containing EcoRI restriction
      site

<400> SEQUENCE: 28
accgaattct cagggctgcg caaggtggcg tagaacgcg                          39

<210> SEQ ID NO 29
<211> LENGTH: 13
<212> TYPE: PRT
<213> ORGANISM: Artificial Sequence
<220> FEATURE:
<223> OTHER INFORMATION: E. coli OmpA signal peptide plus the 1st to the
      5th amino acids of [Ser1]hG-CSF

<400> SEQUENCE: 29

Gly Phe Ala Thr Val Ala Gln Ala Ser Pro Leu Gly Pro
 1               5                   10

<210> SEQ ID NO 30
<211> LENGTH: 30
<212> TYPE: DNA
<213> ORGANISM: Artificial Sequence
<220> FEATURE:
<223> OTHER INFORMATION: Oligonucleotide for preparing [Thr1]hG-CSF

<400> SEQUENCE: 30
accgttgcgc aagctacacc cctgggccct                                    30

<210> SEQ ID NO 31
<211> LENGTH: 30
<212> TYPE: DNA
<213> ORGANISM: Artificial Sequence
<220> FEATURE:
<223> OTHER INFORMATION: Antisense of SEQ ID NO: 30

<400> SEQUENCE: 31
agggcccagg ggtgtagctt gcgcaacggt                                    30

<210> SEQ ID NO 32
<211> LENGTH: 33
<212> TYPE: DNA
<213> ORGANISM: Artificial Sequence
<220> FEATURE:
<223> OTHER INFORMATION: Oligonucleotide for preparing [Ser17]hG-CSF

<400> SEQUENCE: 32
agcttcctgc tcaagtcttt agagcaagtg agg                                33

<210> SEQ ID NO 33
<211> LENGTH: 33
<212> TYPE: DNA
<213> ORGANISM: Artificial Sequence
<220> FEATURE:
<223> OTHER INFORMATION: Antisense of SEQ ID NO: 32

<400> SEQUENCE: 33
cctcacttgc tctaaagact tgagcaggaa gct                                33

<210> SEQ ID NO 34
<211> LENGTH: 33
<212> TYPE: DNA
<213> ORGANISM: Artificial Sequence
<220> FEATURE:
<223> OTHER INFORMATION: Oligonucleotide for preparing [Thr17]hG-CSF

<400> SEQUENCE: 34
agcttcctgc tcaagaccct tagagcaagtg agg                               33

<210> SEQ ID NO 35
<211> LENGTH: 33
<212> TYPE: DNA
<213> ORGANISM: Artificial Sequence
<220> FEATURE:
<223> OTHER INFORMATION: Antisense of SEQ ID NO: 34

<400> SEQUENCE: 35
cctcacttgc tctaaggtct tgagcaggaa gct                                33

<210> SEQ ID NO 36
<211> LENGTH: 33
<212> TYPE: DNA
<213> ORGANISM: Artificial Sequence
<220> FEATURE:
<223> OTHER INFORMATION: Oligonucleotide for preparing [Ala17]hG-CSF

<400> SEQUENCE: 36
agcttcctgc tcaaggcctt agagcaagtg agg                                33

<210> SEQ ID NO 37
<211> LENGTH: 33
<212> TYPE: DNA
<213> ORGANISM: Artificial Sequence
<220> FEATURE:

```
<223> OTHER INFORMATION: Antisense of SEQ ID NO: 36

<400> SEQUENCE: 37
cctcacttgc tctaaggcct tgagcaggaa gct                                    33

<210> SEQ ID NO 38
<211> LENGTH: 33
<212> TYPE: DNA
<213> ORGANISM: Artificial Sequence
<220> FEATURE:
<223> OTHER INFORMATION: Oligonucleotide for preparing [Gly17]hG-CSF

<400> SEQUENCE: 38
agcttcctgc tcaagggctt agagcaagtg agg                                    33

<210> SEQ ID NO 39
<211> LENGTH: 33
<212> TYPE: DNA
<213> ORGANISM: Artificial Sequence
<220> FEATURE:
<223> OTHER INFORMATION: Antisense of SEQ ID NO: 38

<400> SEQUENCE: 39
cctcacttgc tctaagccct tgagcaggaa gct                                    33

<210> SEQ ID NO 40
<211> LENGTH: 33
<212> TYPE: DNA
<213> ORGANISM: Artificial Sequence
<220> FEATURE:
<223> OTHER INFORMATION: Oligonucleotide for preparing [Asp17]hG-CSF

<400> SEQUENCE: 40
agcttcctgc tcaaggactt agagcaagtg agg                                    33

<210> SEQ ID NO 41
<211> LENGTH: 33
<212> TYPE: DNA
<213> ORGANISM: Artificial Sequence
<220> FEATURE:
<223> OTHER INFORMATION: Antisense of SEQ ID NO: 40

<400> SEQUENCE: 41
cctcacttgc tctaagtcct tgagcaggaa gct                                    33

<210> SEQ ID NO 42
<211> LENGTH: 18
<212> TYPE: PRT
<213> ORGANISM: Escherichia coli
<220> FEATURE:
<221> NAME/KEY: SIGNAL
<222> LOCATION: (1)..(18)
<223> OTHER INFORMATION: E. coli Gene III signal peptide

<400> SEQUENCE: 42

Met Lys Lys Leu Leu Phe Ala Ile Pro Leu Val Val Pro Phe Tyr Ser
 1               5                  10                  15

His Ser

<210> SEQ ID NO 43
<211> LENGTH: 21
<212> TYPE: DNA
<213> ORGANISM: Artificial Sequence
<220> FEATURE:
<223> OTHER INFORMATION: Oligonucleotide containing Nco I restriction
      site
```

```
<400> SEQUENCE: 43
tatagccata gcaccatgga g                                              21

<210> SEQ ID NO 44
<211> LENGTH: 21
<212> TYPE: DNA
<213> ORGANISM: Artificial Sequence
<220> FEATURE:
<223> OTHER INFORMATION: Antisense of SEQ ID NO: 43

<400> SEQUENCE: 44
ctccatggtg ctatggctat a                                              21

<210> SEQ ID NO 45
<211> LENGTH: 8
<212> TYPE: PRT
<213> ORGANISM: Artificial Sequence
<220> FEATURE:
<223> OTHER INFORMATION: The 2nd to the 10th amino acids of hG-CSF

<400> SEQUENCE: 45

Pro Leu Gly Pro Ala Ser Ser Leu
  1               5

<210> SEQ ID NO 46
<211> LENGTH: 25
<212> TYPE: DNA
<213> ORGANISM: Artificial Sequence
<220> FEATURE:
<223> OTHER INFORMATION: Oligonucleotide primer coding for the 2nd to
      the 10th amino acids of hG-CSF plus an additional cytosine at its
      5'-end

<400> SEQUENCE: 46 cccccctgggc cctgccagct ccctg                                         25

<210> SEQ ID NO 47
<211> LENGTH: 25
<212> TYPE: DNA
<213> ORGANISM: Artificial Sequence
<220> FEATURE:
<223> OTHER INFORMATION: Antisense of SEQ ID NO: 46

<400> SEQUENCE: 47
cagggagctg gcagggccca ggggg                                          25

<210> SEQ ID NO 48
<211> LENGTH: 10
<212> TYPE: PRT
<213> ORGANISM: Artificial Sequence
<220> FEATURE:
<223> OTHER INFORMATION: E. coli Gene III signal peptide plus the 1st to
      the 5th amino acids of hG-CSF

<400> SEQUENCE: 48

Phe Tyr Ser His Ser Thr Pro Leu Gly Pro
  1               5                  10

<210> SEQ ID NO 49
<211> LENGTH: 9
<212> TYPE: PRT
<213> ORGANISM: Artificial Sequence
<220> FEATURE:
<223> OTHER INFORMATION: The 1st to the 9th amino acids of [Met2,
      Val3]hG-CSF
```

```
<400> SEQUENCE: 49

Thr Met Val Gly Pro Ala Ser Ser Leu
  1               5

<210> SEQ ID NO 50
<211> LENGTH: 33
<212> TYPE: DNA
<213> ORGANISM: Artificial Sequence
<220> FEATURE:
<223> OTHER INFORMATION: Oligonucleotide for preparing [Met2,
      Val3]hG-CSF

<400> SEQUENCE: 50
tacgcgtcca tggtgggccc tgccagctcc ctg                                  33

<210> SEQ ID NO 51
<211> LENGTH: 33
<212> TYPE: DNA
<213> ORGANISM: Artificial Sequence
<220> FEATURE:
<223> OTHER INFORMATION: Antisense of SEQ ID NO: 50

<400> SEQUENCE: 51
cagggagctg gcagggccca ccatggacgc gta                                  33

<210> SEQ ID NO 52
<211> LENGTH: 10
<212> TYPE: PRT
<213> ORGANISM: Artificial Sequence
<220> FEATURE:
<223> OTHER INFORMATION: E. coli Gene III signal peptide plus the 1st to
      the 5th amino acids of [Met2, Val3]hG-CSF

<400> SEQUENCE: 52

Phe Tyr Ser His Ser Thr Met Val Gly Pro
  1               5                  10

<210> SEQ ID NO 53
<211> LENGTH: 23
<212> TYPE: PRT
<213> ORGANISM: Escherichia coli
<220> FEATURE:
<221> NAME/KEY: SIGNAL
<222> LOCATION: (1)..(23)
<223> OTHER INFORMATION: Thermoresistant E. coli enterotoxin II signal
      peptide

<400> SEQUENCE: 53

Met Lys Lys Asn Ile Ala Phe Leu Leu Ala Ser Met Phe Val Phe Ser
  1               5                  10                  15

Ile Ala Thr Asn Ala Tyr Ala
             20

<210> SEQ ID NO 54
<211> LENGTH: 23
<212> TYPE: PRT
<213> ORGANISM: Artificial Sequence
<220> FEATURE:
<223> OTHER INFORMATION: Modified thermoresistant E. coli enterotoxin II
      signal peptide

<400> SEQUENCE: 54

Met Lys Lys Thr Ile Ala Phe Leu Leu Ala Ser Met Phe Val Phe Ser
  1               5                  10                  15

Ile Ala Thr Asn Ala Gln Ala
             20
```

```
<210> SEQ ID NO 55
<211> LENGTH: 96
<212> TYPE: DNA
<213> ORGANISM: Artificial Sequence
<220> FEATURE:
<223> OTHER INFORMATION: Nucleotide sequence coding for the 1st to 32nd
      amino acids of [Ser1, Ser17]hG-CSF
<220> FEATURE:
<221> NAME/KEY: CDS
<222> LOCATION: (1)..(96)

<400> SEQUENCE: 55 tct ccc ctg ggc cct gcc agc tcc ctg ccc cag agc ttc ctg ctc aag      48
Ser Pro Leu Gly Pro Ala Ser Ser Leu Pro Gln Ser Phe Leu Leu Lys
  1               5                  10                  15 tct tta gag caa gtg agg aag atc cag ggc gat ggc gca gcg ctc cag      96
Ser Leu Glu Gln Val Arg Lys Ile Gln Gly Asp Gly Ala Ala Leu Gln
             20                  25                  30

<210> SEQ ID NO 56
<211> LENGTH: 32
<212> TYPE: PRT
<213> ORGANISM: Artificial Sequence
<220> FEATURE:
<223> OTHER INFORMATION: the 1st to 32nd amino acids of [Ser1,
      Ser17]hG-CSF

<400> SEQUENCE: 56

Ser Pro Leu Gly Pro Ala Ser Ser Leu Pro Gln Ser Phe Leu Leu Lys
  1               5                  10                  15

Ser Leu Glu Gln Val Arg Lys Ile Gln Gly Asp Gly Ala Ala Leu Gln
             20                  25                  30

<210> SEQ ID NO 57
<211> LENGTH: 96
<212> TYPE: DNA
<213> ORGANISM: Artificial Sequence
<220> FEATURE:
<223> OTHER INFORMATION: Nucleotide sequence coding for the 1st to the
      32nd amino acids of [Ser1]hG-CSF
<220> FEATURE:
<221> NAME/KEY: CDS
<222> LOCATION: (1)..(96)

<400> SEQUENCE: 57 tct ccc ctg ggc cct gcc agc tcc ctg ccc cag agc ttc ctg ctc aag      48
Ser Pro Leu Gly Pro Ala Ser Ser Leu Pro Gln Ser Phe Leu Leu Lys
  1               5                  10                  15 tgc tta gag caa gtg agg aag atc cag ggc gat ggc gca gcg ctc cag      96
Cys Leu Glu Gln Val Arg Lys Ile Gln Gly Asp Gly Ala Ala Leu Gln
             20                  25                  30

<210> SEQ ID NO 58
<211> LENGTH: 32
<212> TYPE: PRT
<213> ORGANISM: Artificial Sequence
<220> FEATURE:
<223> OTHER INFORMATION: the 1st to the 32nd amino acids of [Ser1]hG-CSF

<400> SEQUENCE: 58

Ser Pro Leu Gly Pro Ala Ser Ser Leu Pro Gln Ser Phe Leu Leu Lys
  1               5                  10                  15

Cys Leu Glu Gln Val Arg Lys Ile Gln Gly Asp Gly Ala Ala Leu Gln
             20                  25                  30
```

```
<210> SEQ ID NO 59
<211> LENGTH: 96
<212> TYPE: DNA
<213> ORGANISM: Artificial Sequence
<220> FEATURE:
<223> OTHER INFORMATION: Nucleotide sequence coding for the 1st to the
      32nd amino acids of [Ser17]hG-CSF
<220> FEATURE:
<221> NAME/KEY: CDS
<222> LOCATION: (1)..(96)

<400> SEQUENCE: 59 aca ccc ctg ggc cct gcc agc tcc ctg ccc cag agc ttc ctg ctc aag      48
Thr Pro Leu Gly Pro Ala Ser Ser Leu Pro Gln Ser Phe Leu Leu Lys
 1               5                  10                  15 tct tta gag caa gtg agg aag atc cag ggc gat ggc gca gcg ctc cag      96
Ser Leu Glu Gln Val Arg Lys Ile Gln Gly Asp Gly Ala Ala Leu Gln
             20                  25                  30

<210> SEQ ID NO 60
<211> LENGTH: 32
<212> TYPE: PRT
<213> ORGANISM: Artificial Sequence
<220> FEATURE:
<223> OTHER INFORMATION: the 1st to the 32nd amino acids of
      [Ser17]hG-CSF

<400> SEQUENCE: 60

Thr Pro Leu Gly Pro Ala Ser Ser Leu Pro Gln Ser Phe Leu Leu Lys
 1               5                  10                  15

Ser Leu Glu Gln Val Arg Lys Ile Gln Gly Asp Gly Ala Ala Leu Gln
             20                  25                  30

<210> SEQ ID NO 61
<211> LENGTH: 96
<212> TYPE: DNA
<213> ORGANISM: Artificial Sequence
<220> FEATURE:
<223> OTHER INFORMATION: Nucleotide sequence coding for the 1st to the
      32nd amino acids of [Thr17]hG--CSF
<220> FEATURE:
<221> NAME/KEY: CDS
<222> LOCATION: (1)..(96)

<400> SEQUENCE: 61 aca ccc ctg ggc cct gcc agc tcc ctg ccc cag agc ttc ctg ctc aag      48
Thr Pro Leu Gly Pro Ala Ser Ser Leu Pro Gln Ser Phe Leu Leu Lys
 1               5                  10                  15 acc tta gag caa gtg agg aag atc cag ggc gat ggc gca gcg ctc cag      96
Thr Leu Glu Gln Val Arg Lys Ile Gln Gly Asp Gly Ala Ala Leu Gln
             20                  25                  30

<210> SEQ ID NO 62
<211> LENGTH: 32
<212> TYPE: PRT
<213> ORGANISM: Artificial Sequence
<220> FEATURE:
<223> OTHER INFORMATION: the 1st to the 32nd amino acids of
      [Thr17]hG--CSF

<400> SEQUENCE: 62

Thr Pro Leu Gly Pro Ala Ser Ser Leu Pro Gln Ser Phe Leu Leu Lys
 1               5                  10                  15

Thr Leu Glu Gln Val Arg Lys Ile Gln Gly Asp Gly Ala Ala Leu Gln
             20                  25                  30

<210> SEQ ID NO 63
```

-continued

<211> LENGTH: 96
<212> TYPE: DNA
<213> ORGANISM: Artificial Sequence
<220> FEATURE:
<223> OTHER INFORMATION: Nucleotide sequence coding for the 1st to the
      32nd amino acids of [Ala17]hG-CSF
<220> FEATURE:
<221> NAME/KEY: CDS
<222> LOCATION: (1)..(96)

<400> SEQUENCE: 63 aca ccc ctg ggc cct gcc agc tcc ctg ccc cag agc ttc ctg ctc aag     48
Thr Pro Leu Gly Pro Ala Ser Ser Leu Pro Gln Ser Phe Leu Leu Lys
 1               5                  10                  15 gcc tta gag caa gtg agg aag atc cag ggc gat ggc gca gcg ctc cag     96
Ala Leu Glu Gln Val Arg Lys Ile Gln Gly Asp Gly Ala Ala Leu Gln
             20                  25                  30

<210> SEQ ID NO 64
<211> LENGTH: 32
<212> TYPE: PRT
<213> ORGANISM: Artificial Sequence
<220> FEATURE:
<223> OTHER INFORMATION: the 1st to the 32nd amino acids of
      [Ala17]hG-CSF

<400> SEQUENCE: 64

Thr Pro Leu Gly Pro Ala Ser Ser Leu Pro Gln Ser Phe Leu Leu Lys
 1               5                  10                  15

Ala Leu Glu Gln Val Arg Lys Ile Gln Gly Asp Gly Ala Ala Leu Gln
             20                  25                  30

<210> SEQ ID NO 65
<211> LENGTH: 96
<212> TYPE: DNA
<213> ORGANISM: Artificial Sequence
<220> FEATURE:
<223> OTHER INFORMATION: Nucleotide sequence coding for the 1st to the
      32th amino acids of [Gly17]hG-CSF
<220> FEATURE:
<221> NAME/KEY: CDS
<222> LOCATION: (1)..(96)

<400> SEQUENCE: 65 aca ccc ctg ggc cct gcc agc tcc ctg ccc cag agc ttc ctg ctc aag     48
Thr Pro Leu Gly Pro Ala Ser Ser Leu Pro Gln Ser Phe Leu Leu Lys
 1               5                  10                  15 ggc tta gag caa gtg agg aag atc cag ggc gat ggc gca gcg ctc cag     96
Gly Leu Glu Gln Val Arg Lys Ile Gln Gly Asp Gly Ala Ala Leu Gln
             20                  25                  30

<210> SEQ ID NO 66
<211> LENGTH: 32
<212> TYPE: PRT
<213> ORGANISM: Artificial Sequence
<220> FEATURE:
<223> OTHER INFORMATION: the 1st to the 32th amino acids of
      [Gly17]hG-CSF

<400> SEQUENCE: 66

Thr Pro Leu Gly Pro Ala Ser Ser Leu Pro Gln Ser Phe Leu Leu Lys
 1               5                  10                  15

Gly Leu Glu Gln Val Arg Lys Ile Gln Gly Asp Gly Ala Ala Leu Gln
             20                  25                  30

<210> SEQ ID NO 67
<211> LENGTH: 96

```
<212> TYPE: DNA
<213> ORGANISM: Artificial Sequence
<220> FEATURE:
<223> OTHER INFORMATION: Nucleotide sequence coding for the 1st to the
      32nd amino acids of [Met2, Val3]hG-CSF
<220> FEATURE:
<221> NAME/KEY: CDS
<222> LOCATION: (1)..(96)

<400> SEQUENCE: 67 aca atg gtc ggc cct gcc agc tcc ctg ccc cag agc ttc ctg ctc aag      48
Thr Met Val Gly Pro Ala Ser Ser Leu Pro Gln Ser Phe Leu Leu Lys
  1               5                  10                  15 tgc tta gag caa gtg agg aag atc cag ggc gat ggc gca gcg ctc cag      96
Cys Leu Glu Gln Val Arg Lys Ile Gln Gly Asp Gly Ala Ala Leu Gln
             20                  25                  30

<210> SEQ ID NO 68
<211> LENGTH: 32
<212> TYPE: PRT
<213> ORGANISM: Artificial Sequence
<220> FEATURE:
<223> OTHER INFORMATION: the 1st to the 32nd amino acids of [Met2,
      Val3]hG-CSF

<400> SEQUENCE: 68

Thr Met Val Gly Pro Ala Ser Ser Leu Pro Gln Ser Phe Leu Leu Lys
  1               5                  10                  15

Cys Leu Glu Gln Val Arg Lys Ile Gln Gly Asp Gly Ala Ala Leu Gln
             20                  25                  30

<210> SEQ ID NO 69
<211> LENGTH: 96
<212> TYPE: DNA
<213> ORGANISM: Artificial Sequence
<220> FEATURE:
<223> OTHER INFORMATION: Nucleotide sequence coding for the 1st to the
      32nd amino acids of [Met2, Val3, Ser17]hG-CSF
<220> FEATURE:
<221> NAME/KEY: CDS
<222> LOCATION: (1)..(96)

<400> SEQUENCE: 69 aca atg gtc ggc cct gcc agc tcc ctg ccc cag agc ttc ctg ctc aag      48
Thr Met Val Gly Pro Ala Ser Ser Leu Pro Gln Ser Phe Leu Leu Lys
  1               5                  10                  15 tct tta gag caa gtg agg aag atc cag ggc gat ggc gca gcg ctc cag      96
Ser Leu Glu Gln Val Arg Lys Ile Gln Gly Asp Gly Ala Ala Leu Gln
             20                  25                  30

<210> SEQ ID NO 70
<211> LENGTH: 32
<212> TYPE: PRT
<213> ORGANISM: Artificial Sequence
<220> FEATURE:
<223> OTHER INFORMATION: the 1st to the 32nd amino acids of [Met2, Val3,
      Ser17]hG-CSF

<400> SEQUENCE: 70

Thr Met Val Gly Pro Ala Ser Ser Leu Pro Gln Ser Phe Leu Leu Lys
  1               5                  10                  15

Ser Leu Glu Gln Val Arg Lys Ile Gln Gly Asp Gly Ala Ala Leu Gln
             20                  25                  30

<210> SEQ ID NO 71
<211> LENGTH: 10
<212> TYPE: DNA
```

-continued

```
<213> ORGANISM: Artificial Sequence
<220> FEATURE:
<223> OTHER INFORMATION: Modified Shine-Dalgarno sequence

<400> SEQUENCE: 71
gaggtgtttt                                                          10
```

US 7,704,709 B2

MODIFIED HUMAN GRANULOCYTE-COLONY STIMULATING FACTOR AND PROCESS FOR PRODUCING SAME

CROSS REFERENCE TO RELATED APPLICATION

This is a Continuation Application of U.S. Ser. No. 10/031,123 filed on Jan. 9, 2002 now abandoned which is a Continuation Application under 35 U.S.C. § 1.111(a) of PCT/KR00/00733 filed on Jul. 7, 2000.

FIELD OF THE INVENTION

The present invention relates to a modified human granulocyte-colony stimulating factor (hG-CSF), a gene encoding said peptide, a vector comprising said gene, a microorganism transformed with said vector and a process for producing the modified hG-CSF using said microorganism.

BACKGROUND OF THE INVENTION

The term colony stimulating factor (CSF) is inclusive of granulocyte/macrophage-colony stimulating factor (GM-CSF), macrophage-colony stimulating factor (M-CSF) and granulocyte-colony stimulating factor (G-CSF), which are produced by T-cells, macrophages, fibroblasts and endothelial cells. GM-CSF stimulates stem cells of granulocyte or macrophage to induce the differentiation thereof and proliferation of granulocyte or macrophage colonies. M-CSF and G-CSF primarily induce the formation of the colonies of macrophage and granulocyte, respectively. In vivo, G-CSF induces the differentiation of bone marrow leucocytes and enhances the function of mature granulocyte and, accordingly, it's clinical importance in treating leukemia has been well established.

Human G-CSF (hG-CSF) is a protein consisting of 174 or 177 amino acids, the 174 amino-acid variety having higher neutrophil-enhancing activity (Morishita, K. et al., J. Biol. Chem., 262, 15208-15213 (1987)). The amino acid sequence of hG-CSF consisting of 174 amino acids is shown in FIG. 1 and there have been many studies for the mass production of hG-CSF by manipulating a gene encoding said hG-CSF.

For instance, Chugai Pharmaceuticals Co., Ltd. (Japan) has disclosed the amino acid sequence of hG-CSF and a gene encoding same (Korean Patent Publication Nos. 91-5624 and 92-2312), and reported a method for preparing proteins having hG-CSF activity by a gene recombination process (Korean Patent Nos. 47178, 53723 and 57582). In this preparation method, glycosylated hG-CSF is produced in a mammalian cell by employing a genomic DNA or cDNA comprising a polynucleotide encoding hG-CSF. The glycosylated hG-CSF has an O-glycosidic sugar chain, but, it is known that said sugar chain is not necessary for the activity of hG-CSF (Lawrence, M. et al., Science, 232, 61 (1986)). Further, it is also well-known that the production of glycosylated hG-CSF employing mammalian cells requires expensive materials and facilities, and therefore, such a process is not economically feasible.

Meanwhile, there have been attempts to produce non-glycosylated hG-CSF by employing a microorganism, e.g., E. coli. In these studies, hG-CSFs having 175 or 178 amino acids having a methionine residue attached at the N-terminus thereof are obtained due to the ATG initiation codon employed in the microorganism. The additional methionine residue, however, causes undesirable immune responses in human body when the recombinant hG-CSF is administered thereto (European Patent Publication No. 256,843). Further, most of the methionine-containing hG-CSFs produced in E. coli are deposited in the cells as insoluble inclusion bodies, and they must be converted to an active form through a refolding process, at a significant loss of yield. In this regard, four of the five Cys residues present in wild-type hG-CSF participate in forming disulfide bonds, while the remaining one contributes to the aggregation of the hG-CSF product during the refolding process to lower the yield.

Recently, in order to solve the problems associated with the production of a foreign protein within a microbial cell, various efforts have been made to develop a method based on efficient secretion of a target protein across the microbial cell membrane into the extra-cellular domain.

For instance, in a method employing a signal peptide, a desired protein is expressed in the form of a fusion protein wherein a signal peptide is added to the N-terminus of the protein. When the fusion protein passes through the cell membrane, the signal peptide is removed by an enzyme and the desired protein is secreted in a mature form. The secretory production method is advantageous in that the produced amino acid sequence is usually identical to the wild-type. However, the yield of a secretory production method is often quite low due to unsatisfactory efficiencies in both the membrane transport and the subsequent purification process. This is in line with the well-known fact that the yield of a mammalian protein produced in a secretory mode in prokaryotes is very low: Hitherto, no microbial method has been reported for the efficient expression and secretion of soluble hG-CSF having no added methionine residue at its N-terminus.

The present inventors have previously reported the use of a new secretory signal peptide prepared by modifying the signal peptide of E. coli thermoresistant enterotoxin II (Korean Patent Laid-open publication No. 2000-19788) in the production of hG-CSF. Specifically, an expression vector comprising a hG-CSF gene attached to the 3'-end of the modified signal peptide of E. coli thermoresistant enterotoxin II was prepared, and biologically active, mature hG-CSF was expressed by employing E. coli transformed with the expression vector. However, most of the expressed hG-CSF accumulated in the cytoplasm rather than in the periplasm.

The present inventors have endeavored further to develop an efficient secretory method for the production of hG-CSF in a microorganism and have found that a modified hG-CSF, which is prepared by replacing at least one amino acid residue, especially, the 17th cysteine residue, of wild-type hG-CSF with other amino acid, retains the biological activity of the wild-type, and that the modified hG-CSF having no methionine residue at the N-terminus thereof can be efficiently expressed and secreted by a microorganism when an appropriate secretory signal peptide is employed.

SUMMARY OF THE INVENTION

Accordingly, it is an object of the present invention to provide a modified human granulocyte-stimulating factor (hG-CSF) which can be efficiently produced using a microorganism.

It is another object of the present invention to provide a gene encoding said peptide and a vector comprising said gene.

It is a further object of the present invention to provide a microorganism transformed with said vector.

It is a still further object of the present invention to provide a process for producing a hG-CGF which is non-attached methionine residue to amino terminus using said microorganism.

In accordance with one aspect of the present invention, there is provided a modified hG-CSF characterized in that at least one of the 1st, 2nd, 3rd and 17th amino acids of wild-type hG-CSF is replaced by another amino acid.

BRIEF DESCRIPTION OF THE DRAWINGS

The above and other objects and features of the present invention will become apparent from the following description of the invention taken in conjunction with the following accompanying drawings; which respectively show:

FIG. 1: the nucleotide and amino acid sequences of wild-type human granulocyte-stimulating factor composed of 174 amino acids residues (SEQ ID NOS: 1 and 2);

DETAILED DESCRIPTION OF THE INVENTION

Figure 2:
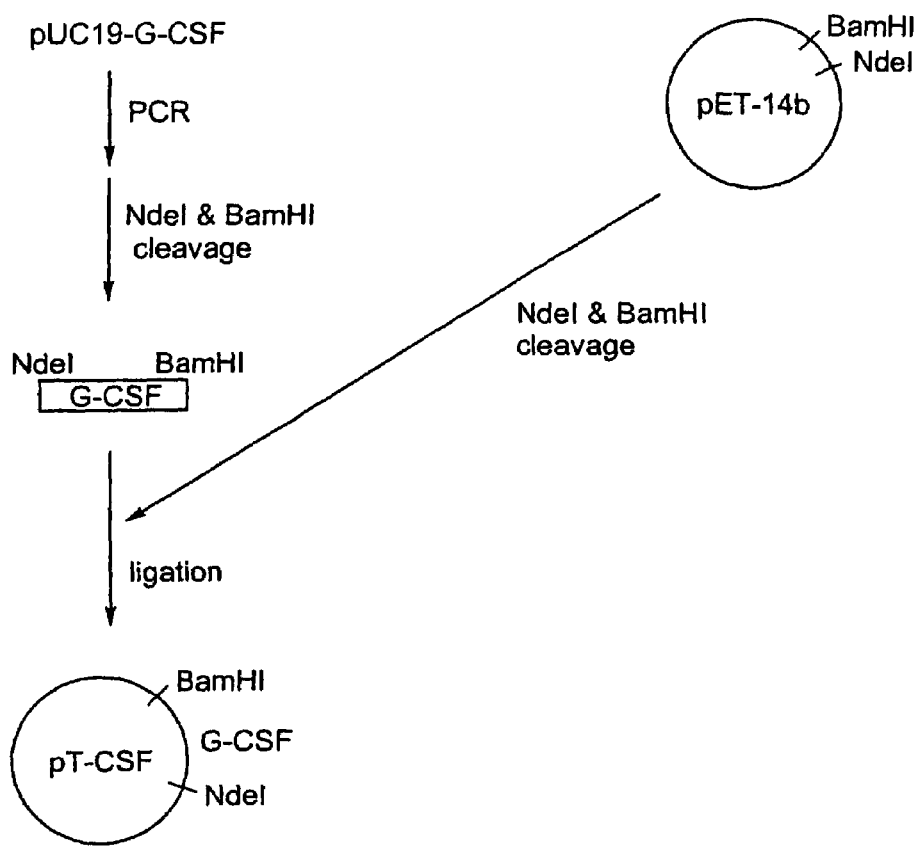
FIG. 2: the procedure for constructing vector pT-CSF.

The modified hG-CSFs of present invention are derived by replacing one or more of the amino acids of wild-type hG-CSF (SEQ ID NO: 2), preferably the 1st, 2nd, 3rd and 17th amino acids thereof, by other amino acids. More preferred are those obtained by replacing the 17th amino acid of hG-CSF with an amino acid which is uncharged at neutral pH. Specific examples of preferred modified hG-CSFs have the amino acid sequence of wild-type hG-CSF, except that:

(a) the 1st amino acid is Ser;
(b) the 1st amino acid is Ser and the 17th amino acid is X;
(c) the 2nd amino acid is Met and the 3rd amino acid is Val;
(d) the 2nd amino acid is Met, the 3rd amino acid is Val and the 17th amino acid is X; or
(f) the 17th amino acid is X, wherein X is an amino acid which is not charged at neutral pH, preferably Ser, Thr, Ala or Gly, more preferably Ser.

Four of the five Cys residues of hG-CSF participate in forming disulfide bonds, while the 17th Cys residue remains unbonded in the natural state. However, when a large amount of hG-CSF is expressed in recombinant cells, the 17th Cys residue gets involved in inter-molecular disulfide bond formation, leading to the accumulation of agglomerated hG-CSFs in the cytoplasm. However, the inventive modified hG-CSF having an amino acid other than Cys at the 17th position is free of such problem and can be effectively produced by a secretory method using an appropriately transformed microorganism.

The modified hG-CSF of the present invention may be encoded by a gene comprising a nucleotide sequence deduced from the modified hG-CSF amino acid sequence according to the genetic code. It is known that several different codons encoding a specific amino acid may exist due to the codon degeneracy, and, therefore, the present invention includes in its scope all nucleotide sequences deduced from the modified hG-CSF amino acid sequence. Preferably, the modified hG-CSF gene sequence includes one or more preferred codons of E. coli.

The gene thus prepared may be inserted to a conventional vector to obtain an expression vector, which may, in turn, be introduced into a suitable host, e.g., an E. coli. The expression vector may further comprise a signal peptide. Representative signal peptides include a thermoresistant E. coli. enterotoxin II signal peptide (SEQ ID NO: 53), a modified thermoresistant E. coli enterotoxin II signal peptide (SEQ ID NO: 54), a beta lactamase signal peptide (SEQ ID NO: 24), Gene III signal peptide (SEQ ID NO: 42) or modified peptide thereof, but these do not limit the signal peptides which may be used in the present invention. The promoter used in preparing the expression vector of present invention may be any of those which can express a heterologous protein in a microorganism host. Specially, lac, Tac, and arabinose promoter is preferred when the heterologous protein is expressed from E. coli.

Exemplary expression vector of the present invention includes pT14SS1SG, pT14SS1S17SEG, pTO1SG, pTO1S17SG, pTO17SG, pTO17TG, pTO17AG, pTO17GG, pBAD2M3VG, pBAD17SG and pBAD2M3V17SG.

The expression vectors of the present invention may be introduced into microorganism, e.g., E. coli BL21(DE3) (Novagen), E. coli XL-1 blue (Novagen) according to a conventional transformation method (Sambrook et al., the supra) to obtain transformants E. coli BL21(DE3)/pT14SS1SG(HM 10310), E. coli BL21(DE3)/pT14SS1S17SEG(HM 10311), E. coli BL21(DE3)/pTO1SG(HM 10409), E. coli BL21 (DE3)/pTO1S17SG(HM 10410), E. coli BL21(DE3)/ pTO17SG(HM 10411), E. coli BL21(DE3)/pTO17TG(HM 10413), E. coli BL21(DE3)/pTO17AG(HM 10414), E. coli BL21(DE3)/pTO17GG(HM 10415), E. coli BL21(DE3)/ pBAD2M3VG(HM 10510), E. coli BL21(DE3)/pBAD17SG (HM 10511) and E. coli BL21(DE3)/pBAD2M3V17SG(HM 10512). Among the transformed microorganism, preferred are transformants E. coli BL21(DE3)/pT14SS1S17SEG(HM 10311), E. coli BL21(DE3)/pTO1S17SG(HM 10410), E. coli BL21(DE3)/pTO17SG(HM 10411) and E. coli BL21(DE3)/ pBAD2M3VG(HM 10510) which were deposited with Korean Culture Center of Microorganisms(KCCM) (Address; Department of Food Engineering, College of Eng., Yonsei University, Sodaemun-gu, Seoul 120-749, Republic of Korea) on Mar. 24, 1999 under accession numbers KCCM-10154, KCCM-10151, KCCM-10152 and KCCM-10153, respectively, in accordance with the terms of the Budapest Treaty on the International Recognition of the Deposit of Microorganism for the Purpose of Patent Procedure.

The modified hG-CSF protein of the present invention may be produced by culturing the transformant microorganism to express the gene encoding the modified hG-CSF protein and secrete the modified hG-CSF, protein to periplasm; and recovering the modified hG-CSF protein from the periplasm. The transformant microorganism may be cultured in accordance with a conventional method (Sambrook et al., the supra). The microorganism culture may be centrifuged or filtered to collect the microorganism secreting the modified hG-CSF protein. The transformed microorganism may be disrupted according to a conventional method (Ausubel, F. M. et al., *Current Protocols in Molecular Biology*, (1989)) to obtain a periplasmic solution. For example, the microorganism may be disrupted in a hypotonic solution, e.g., distilled water, by an osmotic shock. Recovery of the modified hG-CSF in the periplasmic solution may be conducted by a conventional method (Sambrook et al., the supra), e.g., ion exchange chromatography, gel filtration column chromatography or immune column chromatography. For example, hG-CSF may be purified by sequentially conducting CM-Sepharose column chromatograph and Phenyl Sepharose column chromatography.

The modified hG-CSF protein produced according to the present invention is not methionylated at the N-terminus and has biological activity which is equal to, or higher than, that of wild-type hG-CSF. Therefore, it may be used as is in various applications The following Examples are intended to further illustrate the present invention without limiting its scope.

EXAMPLE 1

Preparation of a Gene Encoding hG-CSF

A cDNA gene encoding hG-CSF was prepared by carrying out PCR using as an hG-CSF template (R&D system, USA). The primers used are those described in U.S. Pat. No. 4,810,643.

To prepare a cDNA gene encoding mature hG-CSF, vector pUC19-G-CSF (Biolabs, USA) was subjected to PCR using the primers of SEQ ID NOS: 3 and 4. The primer of SEQ ID NO: 3 was designed to provide an NdeI restriction site (5'-CATATG-3') upstream from the first amino acid (threonine) codon of mature hG-CSF, and the primer of SEQ ID NO: 4, to provide a BamHI restriction site (5'-GGATCC-3') downstream from the termination codon thereof.

The amplified hG-CSF gene was cleaved with NdeI and BamHI to obtain a gene encoding mature hG-CSF. The hG-CSF gene was inserted at the NdeI/BamHI section of vector pET14b (Novagen, USA) to obtain vector pT-CSF.

FIG. 2 shows the above procedure for constructing vector pT-CSF.

EXAMPLE 2

Construction of a Vector Containing the Gene Encoding E. coli Enterotoxin II Signal Peptide and a Modified hG-CSF (Step 1) Cloning E. coli Enterotoxin II Signal Peptide Gene To prepare E. coli enterotoxin II signal peptide gene, the pair of complementary oligonucleotides having SEQ ID NOS: 5 and 6 were designed based on the nucleotide sequence of E. coli enterotoxin II signal peptide, and synthesized using DNA synthesizer (Model 380B, Applied Biosystem, USA).

The above oligonucleotides were designed to provide BspHI restriction site (complementary sites to an NcoI restriction sites) upstream from the initiation codon of E. coli enterotoxin II and an MluI restriction site introduced by a silent change at the other end.

Both oligonucleotides were annealed at 95° C. to obtain blunt-ended DNA fragments having a nucleotide sequence encoding E. coli enterotoxin II signal peptide (STII gene).

The STII gene was inserted at the SmaI site of vector pUC19 (Biolabs, USA) to obtain vector pUC 19ST.

(Step 2) Preparation of a Gene Encoding STII/hG-CSF

To prepare a gene encoding STII/hG-CSF, vector pT-CSF obtained in Preparation Example 1 was subjected to PCR using the primers of SEQ ID NOS: 7 and 8. The primer of SEQ ID NO: 7 was designed to substitute Ser codon for the first codon of hG-CSF, and the primer of SEQ ID NO: 8, to provide a BamHI restriction site (5'-GGATCC-3') downstream from the termination codon thereof.

The amplified DNA fragments were cleaved with MluI and BamHI, and then inserted at the MluI/BamHI section of pUC19ST obtained in Step 1 to obtain vector pUC19S1SG. Vector pUC19S1SG thus obtained contained a gene encoding an STII/hG-CSF (designated STII-hG-CSF gene).

Vector pUC19S1SG was cleaved with BspHI and BamHI to obtain a DNA fragment (522 bp). The DNA fragment was inserted at the NcoI/BamHI section of vector pET14b (Novagen, USA) to obtain vector pT14S1SG.

Figure 3:
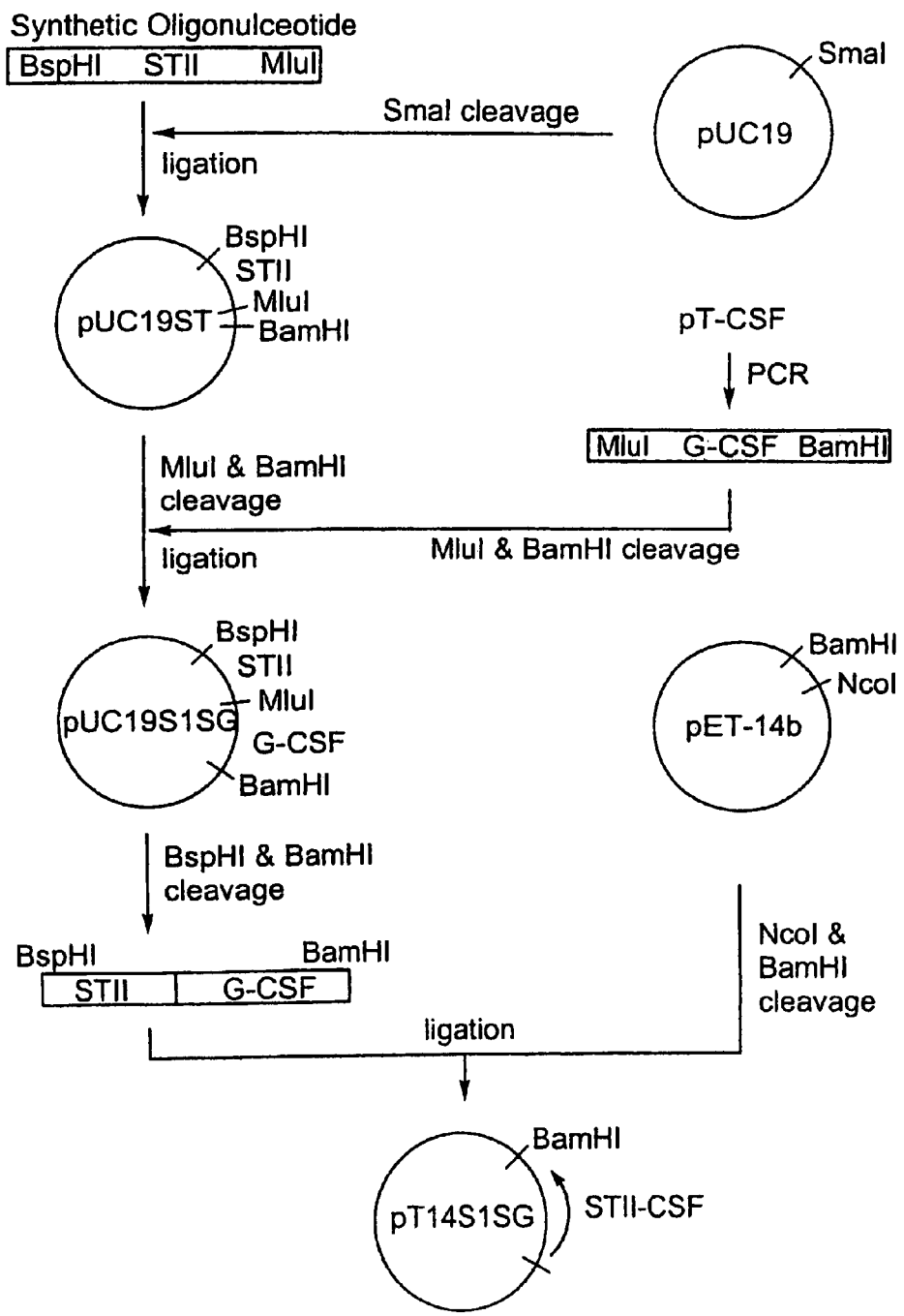
FIG. 3: the procedure for constructing vector pT14S1SG.

FIG. 3 depicts the above procedure for constructing vector pT14S1SG.

(Step 3) Addition of E. coli Enterotoxin II Shine-Dalgarno Sequence to STII-hG-CSF Gene Vector pT14S1SG obtained in Step 2 was subjected to PCR using the primers of SEQ ID NOS: 9 and 10. The primer of SEQ ID NO: 9 was designed to provide an E. coli enterotoxin II Shine-Dalgano sequence (designated STII SD sequence) and an XbaI restriction site, and the primer of SEQ ID NO: 10, to provide a BamHI restriction site downstream from the termination codon of mature hG-CSF to obtain a DNA fragment (STII SD-STII-hCSF) containing a STII SD and STII-hG-CSF gene.

The STII SD-STII-hG-CSF fragment was cleaved with XbaI and BamHI, and then inserted at the XbaI/BamHI section of vector pET14b (Novagen, USA) to obtain vector pT14SS1SG.

Figure 4:
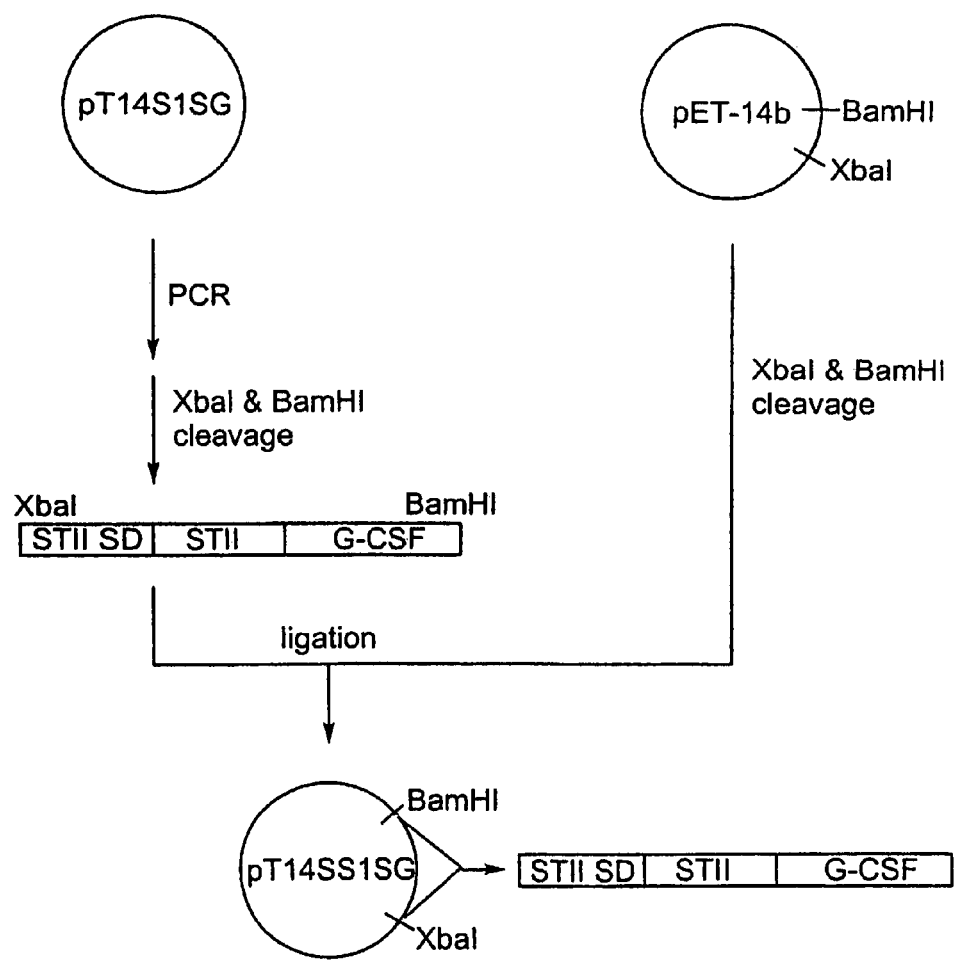
FIG. 4: the procedure for constructing vector pT14SS1SG.

FIG. 4 displays the above procedure for constructing vector pT14SS1SG.

E. coli BL21(DE3) (Stratagene, USA) was transformed with vector pT14SS1SG to obtain a transformant designated E. coli HM 10310.

(Step 4) Construction of a Vector Containing a Gene Encoding STII/hG-CSF Fusion Protein The first codon of the modified hG-CSF gene of plasmid pT14SS1SSG obtained in Step 3 was replaced by Thr in accordance with a site-directed mutagenesis (Papworth, C. et al., *Strategies*, 9, 3 (1996)), which was conducted by PCR of the plasmid with a sense primer (SEQ ID NO: 12) having a modified nucleotide sequence, a complementary antisense primer (SEQ ID NO: 13), and pfu (Stragene, USA).

The amplified DNA fragment was recovered and restriction enzyme DpnI was added thereto to remove unconverted plasmids.

E. coli XL-1 blue (Novagen, USA) was transformed with the modified plasmid. The base sequence of the DNA recovered from transformed colonies was determined, and thus obtained was plasmid pT14SSG which contained a gene having Thr in place of the first amino acid of hG-CSF (SEQ ID NO: 11).

```
    -5  -4  -3  -2  -1  +1  +2  +3  +4  +5
                                    (SEQ ID NO: 11)
    Thr Asn Ala Tyr Ala Thr Pro Leu Gly Pro (SEQ ID NO: 12)
    ACA-AAT-GCC-TAC-GCG-ACA-CCC-CTG-GGC-CCT (SEQ ID NO: 13)
    TGT-TTA-CGG-ATG-CGC-TGT-GGG-GAC-CCG-GGA
```

E. coli BL21(DE3) (Stratagene, USA) was transformed with vector pT14SSG to obtain a transformant designated E. coli HM 10301.

(Step 5) Construction of a Vector Containing a Gene Encoding Modified STII/hG-CSF Vector pT14SSG obtained in Step 4 was subjected to PCR using the complementary primers of SEQ ID NOS: 15 and 16, which were designed to substitute Thr codon for the 4th codon of STII in accordance with the procedure of Step 4 to obtain a modified plasmid.

E. coli XL-1 blue (Novagen, USA) was transformed with the modified plasmid. The base sequence of the DNA recovered from transformed colonies was determined, and thus obtained was plasmid which contained a gene having Thr in place of the 4th amino acid of STII (SEQ ID NO: 14).

```
                                     (SEQ ID NO: 14)
         Met Lys Lys Thr Ile Ala Phe Leu (SEQ ID NO: 15)
5'-GG-TGT-TTT-ATG-AAA-AAG-ACA-ATC-GCA-TTT-CTT-C-3'

(SEQ ID NO: 16)
3'-CC-ACA-AAA-TAC-TTT-TTC-TGT-TAG-CGT-AAA-GAA-G-5'
```

The plasmid thus obtained was cleaved with XbaI and MluI, and then inserted at the XbaI/MluI section of vector pT14SSG obtained in step 4 to obtain vector pT14SSG-4T.

(Step 6) Construction of a Vector Containing a Gene Encoding Modified STII/hG-CSF Vector pT14SSG-4T obtained in Step 5 was subjected to PCR using the complementary primers of SEQ ID NOS: 18 and 19, which were designed to substitute Gln codon for the 22nd codon of STII in accordance with the procedure of Step 4 to obtain a modified plasmid.

E. coli XL-1 blue (Novagen, USA) was transformed with the modified plasmid. The base sequence of the DNA recovered from transformed colonies was determined, and thus obtained was plasmid pT14SSG-4T22Q which contained a gene having Gln in place of the 22nd amino acid of STII (SEQ ID NO: 17).

```
                                     (SEQ ID NO: 17)
         ASN Ala Gln Ala Thr Pro Leu Gly (SEQ ID NO: 18)
5'-CA-AAT-GCC-CAA-GCG-ACA-CCC-CTG-GGC-3'

(SEQ ID NO: 19)
3'-GT-TTA-CGG-GTT-CGC-TGT-GGG-GAC-CCG-5'
```

(Step 7) Construction of a Vector Containing a Modified STII SD and a Gene Encoding Modified STII/hG-CSF Vector pT14SSG-4T22Q obtained in Step 6 was subjected to PCR using the complementary primers of SEQ ID NOS: 20 and 21 in accordance with the procedure of Step 4 to obtain vector pT140SSG-4T22Q having the six nucleotide sequences between the STII SD sequence (GAGG) and the initiation codon of STII (modified STII SD of SEQ ID NO: 71).

Figure 5:
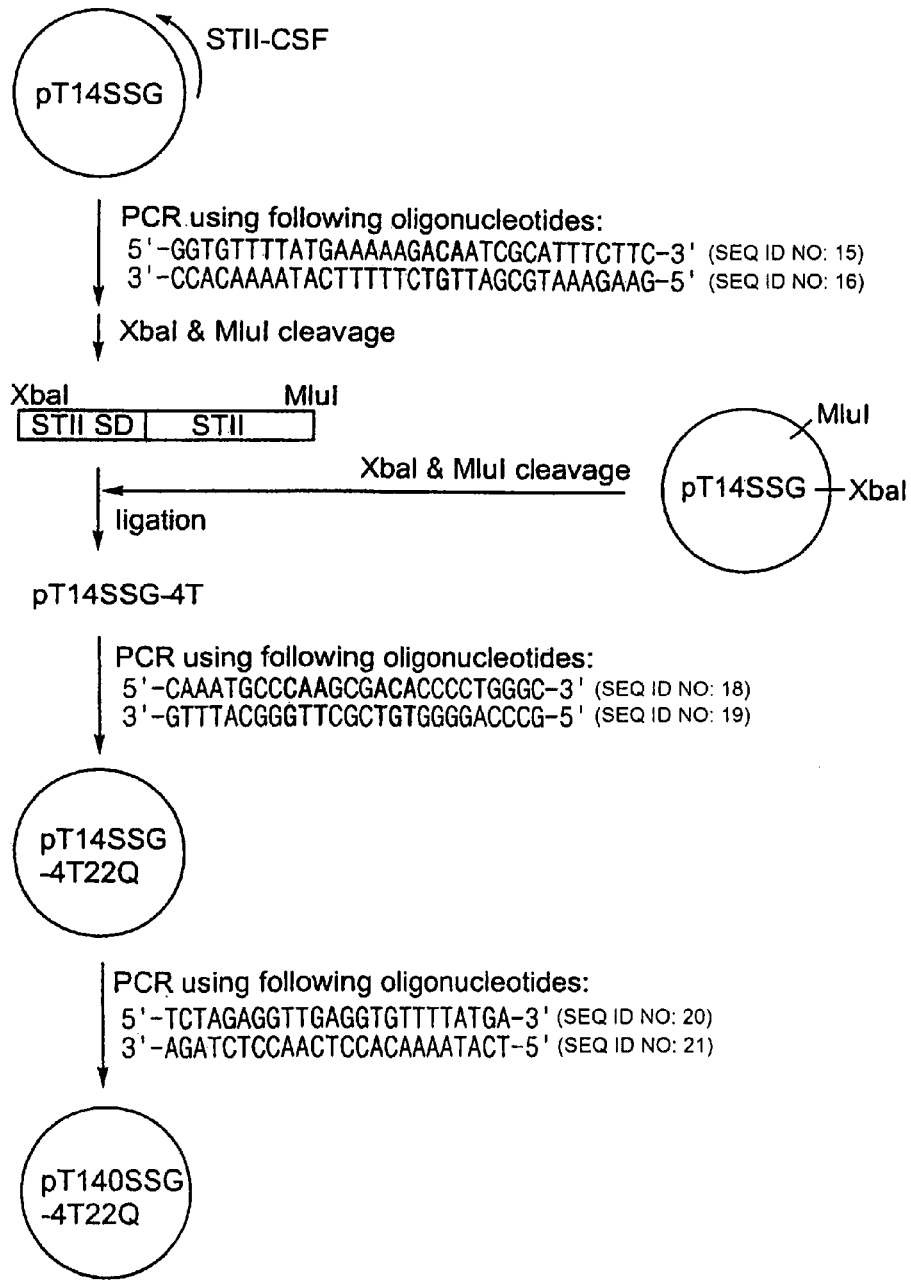
FIG. 5: the procedure for constructing vector pT140SSG-4T22Q.

FIG. 5 represents the above procedure for constructing vector pT140SSG-4T22Q.

E. coli BL21(DE3) was transformed with vector pT140SSG-4T22Q to obtain a transformant designated E. coli HM 10302.

EXAMPLE 3

Construction of a Vector Containing a Gene Encoding Modified hG-CSF

To prepare a modified hG-CSF gene, S1 oligomer (SEQ ID NO: 22) having E. coli-preferred codons and Ser in place of the 17th amino acid of hG-CSF and AS1 oligomer (SEQ ID NO: 23) were synthesized using DNA synthesizer (Model 380B, Applied Biosystem, USA).

0.5 µl (50 pmole) quantities of the oligonucleotides were reacted at 95° C. for 15 min. and kept until 35° C. for 3 hours. The mixture was precipitated in ethanol and subjected to gel electrophoresis (SDS-PAGE) to obtain a cohesive ended double strand(ds) oligomer.

The plasmid pT14SS1SG obtained in step 3 of Example 2 was cleaved with ApaI and BstXI, and then ligated with the adhesive-ended ds oligomer, to obtain vector pT14SS1S17SEG. Vector pT14SS1S17SEG contained a gene encoding hG-CSF having E. coli-preferred codons at the amino terminus and Ser in place of the 1st and 17th amino acids of hG-CSF, respectively.

Figure 6:
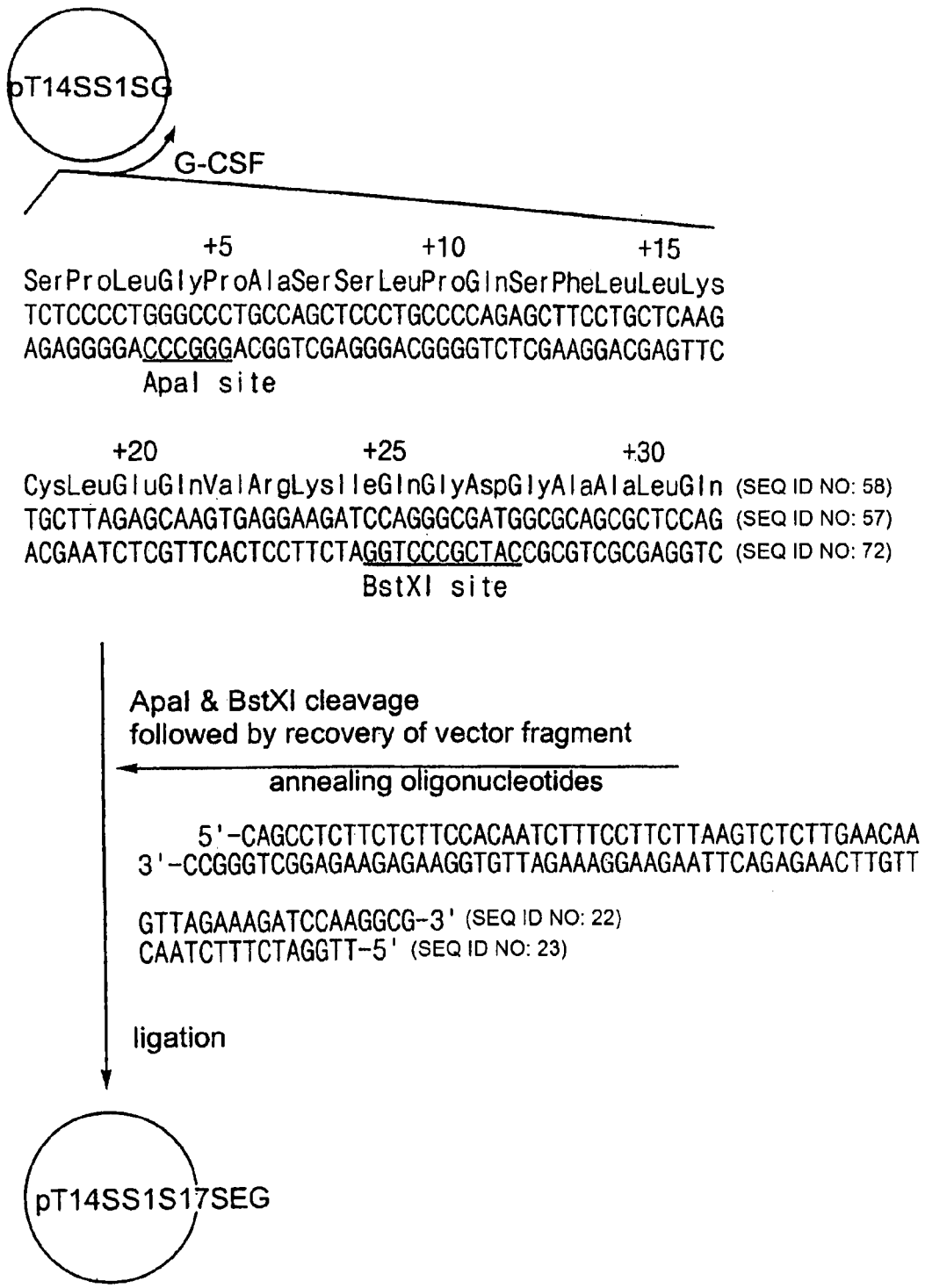
FIG. 6: the procedure for constructing vector pT14SS1S17SEG.

FIG. 6 illustrates the above procedure for constructing vector pT140SS1S17SEG.

E. coli BL21(DE3) was transformed with vector pT14SS1S17SEG to obtain a transformant designated E. coli HM 10311, which was deposited with Korean Culture Center of Microorganisms (KCCM) on Mar. 24, 1999 under accession number KCCM-10154.

EXAMPLE 4

Construction of Vector Containing a Gene Encoding E. coli OmpA Signal Peptide and Modified hG-CSF A vector containing a gene encoding Tac promoter and OmpA signal peptide (SEQ ID NO: 24) as well as a gene encoding modified hG-CSF was prepared as follows:

```
                                     (SEQ ID NO: 24)
Met-Lys-Lys-Thr-Ala-Ile-Ala-Ile-Ala-Val-Ala-Leu-
Ala-Gly-Phe-Ala-Thr-Val-Ala-Gln-Ala- (SEQ ID NO: 25)
--GTT-GCG-CAA-GCT-TCT-CGA--

(SEQ ID NO: 26)
--CAA-CGC-GTT-CGA-AGA-GCT--
         HindIII restriction site
```

Vector pT-CSF obtained in Example 1 was subjected to PCR using a primer (SEQ ID NO: 27) designed to substitute Ser codon for the 1st codon of hG-CSF and another primer (SEQ ID NO: 28), to provide an EcoRI restriction site (5'-GAATTC-3') downstream from the termination codon thereof to obtain a DNA fragment containing a gene encoding modified hG-CSF.

The DNA fragment was cleaved with HindIII and EcoRI, and then inserted at the HindIII/EcoRI section of vector pFlag.CTS (Eastman, USA) to obtain vector pTO1SG which contained a gene encoding E. coli OmpA signal peptide and modified hG-CSF (SEQ ID NO: 29).

Figure 7:
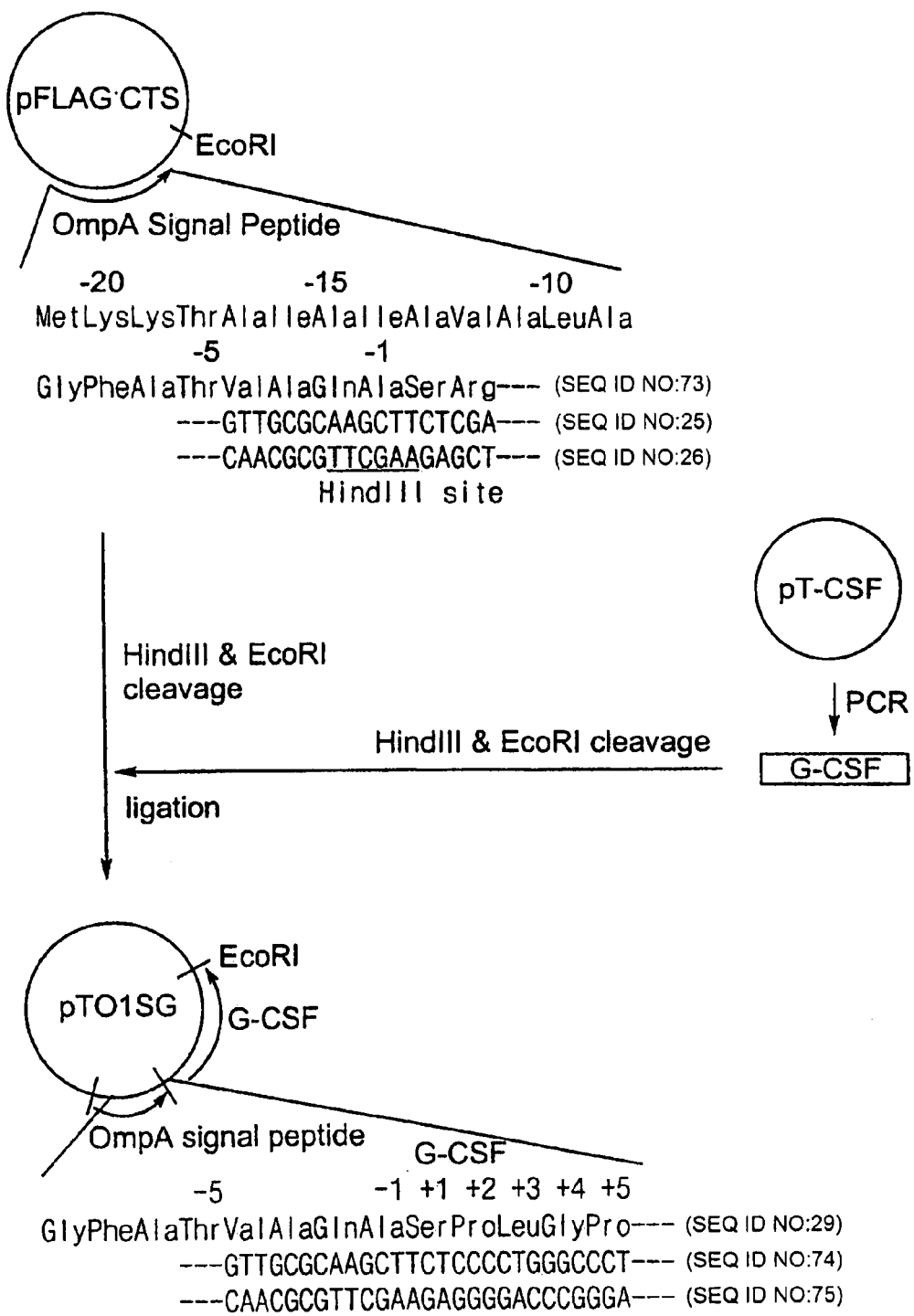
FIG. 7: the procedure for constructing vector pTO1SG.

FIG. 7 exhibits the above procedure for constructing vector pTO1SG.

*E. coli* BL21(DE3) (Stratagene, USA) was transformed with vector pTO1SG to obtain a transformant designated *E. coli* HM 10409.

EXAMPLE 5

Construction of a Vector Containing a Gene Encoding *E. coli* OmpA Signal Peptide and Modified hG-CSF The first codon of the modified hG-CSF gene of plasmid pTO1SG obtained in Example 4 was replaced by Thr in accordance with site-directed mutagenesis (Papworth, C. et al., *Strategies*, 9, 3 (1996)), by conducting PCR of the plasmid pTO1SG obtained in Example 4 with a sense primer (SEQ ID NO: 30) designed to substitute Thr codon for the 1st codon of hG-CSF and a complementary antisense primer (SEQ ID NO: 31).

*E. coli* XL-1 blue (Novagen, USA) was transformed with the modified plasmid. The base sequence of the DNA recovered from transformed colonies was determined, and thus obtained plasmid pTOG which contained a gene having Thr in place of the first amino acid of hG-CSF.

*E. coli* BL21(DE3) (Stratagene, USA) was transformed with vector pTOG to obtain a transformant designated *E. coli* HM 10401.

EXAMPLE 6

Production of Modified hG-CSFs (a) Production of [Ser1, Ser17] hG-CSF

Vector pTO1SG obtained in Example 4 was subjected to PCR using a sense primer (SEQ ID NO: 32) designed to substitute Ser codon for the 17th codon of hG-CSF and a complementary antisense primer (SEQ ID NO: 33) in accordance with the procedure of Step 4 of Example 2 to obtain a modified plasmid.

*E. coli* XL-1 blue (Novagen, USA) was transformed with the modified plasmid. The base sequence of the DNA recovered from transformed colonies was determined and thus obtained was plasmid pTO1S17SG which contained a gene having Ser in place of the 1st and 17th amino acids of hG-CSF.

*E. coli* BL21(DE3) (Stratagene, USA) was transformed with vector pTO1S17SG to obtain a transformant designated *E. coli* HM 10410, which was deposited with Korean Culture Center of Microorganisms (KCCM) on Mar. 24, 1999 under accession number KCCM-10151.

(b) Production of [Ser17] hG-CSF

Vector pTOG obtained in Example 5 was subjected to PCR using a sense primer (SEQ ID NO: 32) designed to substitute Ser codon for the 17th codon of hG-CSF and a complementary antisense primer (SEQ ID NO: 33) in accordance with the procedure of Step 4 of Example 2 to obtain a modified plasmid.

*E. coli* XL-1 blue (Novagen, USA) was transformed with the modified plasmid. The base sequence of the DNA recovered from transformed colonies was determined, and thus obtained was plasmid pTO17SG which contained a gene having Ser in place of the 17th amino acid of hG-CSF.

*E. coli* BL21(DE3) (Stratagene, USA) was transformed with vector pTO17SG to obtain a transformant designated *E. coli* HM 10411, which was deposited with Korean Culture Center of Microorganisms (KCCM) on Mar. 24, 1999 under accession number KCCM-10152.

(c) Production of [Thr17] hG-CSF

Vector pTOG obtained in Example 5 was subjected to PCR using a sense primer (SEQ ID NO: 34) designed to substitute Thr codon for the 17th codon of hG-CSF and a complementary antisense primer (SEQ ID NO: 35) in accordance with the procedure of Step 4 of Example 2 to obtain a modified plasmid.

*E. coli* XL-1 blue (Novagen, USA) was transformed with the modified plasmid. The base sequences of the DNA recovered from transformed colonies was determined, and thus obtained was plasmid pTO17TG which contained a gene having Thr in place of the 17th amino acid of hG-CSF.

*E. coli* BL21(DE3) (Stratagene, USA) was transformed with vector pTO17TG to obtain a transformant designated *E. coli* HM 10413.

(d) Production of [Ala17] hG-CSF

Vector pTOG obtained in Example 5 was subjected to PCR using a sense primer (SEQ ID NO: 36) designed to substitute Ala codon for the 17th codon of hG-CSF and a complementary antisense primer (SEQ ID NO: 37) in accordance with the procedure of Step 4 of Example 2 to obtain a modified plasmid.

*E. coli* XL-1 blue (Novagen, USA) was transformed with the modified plasmid. The base sequence of DNA recovered from transformed colonies was determined, and thus obtained was plasmid pTO17AG which contained a gene having Ala in place of the 17th amino acid of hG-CSF.

*E. coli* BL21(DE3) (Stratagene, USA) was transformed with vector pTO17AG to obtain a transformant designated *E. coli* HM 10414.

(e) Production of [Gly17] hG-CSF

Vector pTOG obtained in Example 5 was subjected to PCR using a sense primer (SEQ ID NO: 38) designed to substitute Gly codon for the 17th codon of hG-CSF and a complementary antisense primer (SEQ ID NO: 39) in accordance with the procedure of Step 4 of Example 2 to obtain a modified plasmid.

*E. coli* XL-1 blue (Novagen, USA) was transformed with the modified plasmid. The base sequence of the DNA recovered from transformed colonies was determined, and thus obtained was plasmid pTO17GG which contained a gene having Gly in place of the 17th amino acids of hG-CSF.

*E. coli* BL21(DE3) (Stratagene, USA) was transformed with vector pTO17GG to obtain a transformant designated *E. coli* HM 10415.

(f) Production of [Asp17] hG-CSF

Vector pTOG obtained in Example 5 was subjected to PCR using a sense primer (SEQ ID NO: 40) designed to substitute Asp codon for the 17th codon of hG-CSF and a complementary antisense primer (SEQ ID NO: 41) in accordance with the procedure of Step 4 of Example 2 to obtain a modified plasmid.

*E. coli* XL-1 blue (Novagen, USA) was transformed with the modified plasmid. The base sequence of the DNA recovered from transformed colonies was determined, and thus obtained was plasmid pTO17APG which contained a gene having Asp in place of the 17th amino acids of hG-CSF.

*E. coli* BL21(DE3) (Stratagene, USA) was transformed with vector pTO17APG to obtain a transformant designated *E. coli* HM 10416.

EXAMPLE 7

Construction of a Vector Containing a Gene Encoding E. coli Gene III Signal Peptide and Modified hG-CSF (a) Construction of a Vector Containing a Gene Encoding Arabinose Promoter and E. coli Gene III Signal Peptide A vector containing a gene encoding arabinose promoter and E. coli Gene III signal peptide (SEQ ID NO: 42) as well as a gene encoding modified hG-CSG was prepared as follows:

(SEQ ID NO: 42)
Met-Lys-Lys-Leu-Leu-Phe-Ala-Ile-Pro-Leu-Val-Val-

Pro-Phe-Tyr-Ser-His-Ser- (SEQ ID NO: 43)
-TAT-AGC-CAT-AGC-ACC-ATG-GAG- (SEQ ID NO: 44)
-ATA-TCG-GTA-TCG-TGG-TAC-CTC-
NcoI restriction site Plasmid pBAD.gIIIA (Invitrogen, USA) containing a gene encoding arabinose promoter and Gene III signal peptide was cleaved with NcoI, and single stranded DNAs were removed with Klenow DNA polymerase to obtain a blunt-ended double stranded DNA, which was then cleaved with BglII to obtain a vector fragment having both blunt end and a cohesive end.

Vector pT-CSF obtained in Example 1 was subjected to PCR using a sense primer (SEQ ID NO: 46) having a nucleotide sequence coding for the 2nd to the 9th amino acids of hG-CSF (SEQ ID NO: 45) and a complementary antisense primer (SEQ ID NO: 47) in accordance with the procedure of Step 4 of Example 2 to obtain a blunt-ended DNA fragment containing hG-CSF gene and a BamHI restriction site in the carboxy terminus. The fragment then was cleaved with BamHI to obtain hG-CSF gene fragment having both a blunt end and a cohesive end.

(SEQ ID NO 45)
Pro Leu Gly Pro Ala Ser Ser Leu (SEQ ID NO 46)
5' -C-CCC-CTG-GGC-CCT-GCC-AGC-TCC-CTG-3'

(SEQ ID NO 47)
3' -G-GGG-GAC-CCG-GGA-CGG-TCG-AGG-GAC-5'

The hG-CSF gene fragment as inserted into the vector obtained above to obtain vector pBADG which contained a gene encoding E. coli Gene III signal peptide and hG-CSF (SEQ ID NO: 48).

Figure 8:
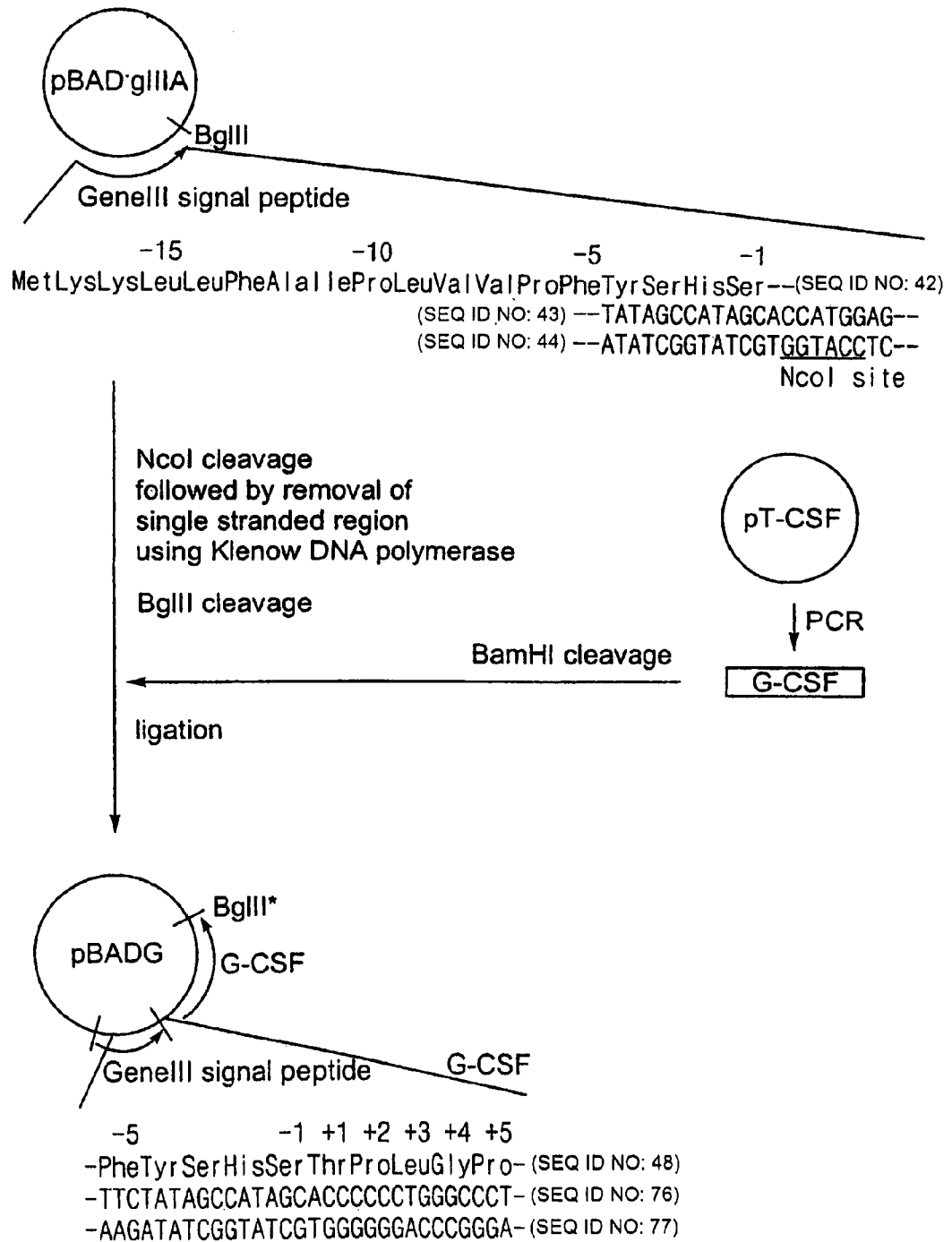
FIG. 8: the procedure for constructing vector pBADG.

FIG. 8 describes the above procedure for constructing vector pBADG.

E. coli BL21(DE3) (Stratagene, USA) was transformed with vector pBADG to obtain a transformant designated E. coli HM 10501.

(b) Production of [Met2, Val3] hG-CSF

Plasmid pBAD.gIIIA (Invitrogen, USA) was cleaved with NcoI and BglII to obtain a fragment having two cohesive ends.

Vector pT-CSF obtained in Example 1 was subjected to PCR using a sense primer (SEQ ID NO: 50) having a nucleotide sequence coding for the 1st to the 9th amino acids of [Met2, Val3] hG-CSF (SEQ ID NO: 49) and a complementary antisense primer (SEQ ID NO: 51) in accordance with the procedure of Step 4 of Example 2 to obtain a blunt-ended DNA fragment containing hG-CSF gene and a BamHI restriction site in the carboxy terminus, which was then was cleaved with NcoI and BamHI to obtain a hG-CSF gene fragment having two cohesive ends.

(SEQ ID NO: 49)
Thr Met Val Gly Pro Ala Ser Ser Leu (SEQ ID NO: 50)
5'-TAC-GCG-TCC-ATG-GTG-GGC-CCT-GCC-AGC-TCC-CTG-3'

(SEQ ID NO: 51)
3'-ATG-CGC-AGG-TAC-CAC-CCG-GGA-CGG-TCG-AGG-GAC-5'
NcoI restriction site The hG-CSF gene fragment was inserted into the vector obtained above to obtain vector pBAD2M2VG contained a gene coding E. coli Gene III signal peptide, and Met and Val in place of the 2nd and 3rd amino acids of hG-CSF (SEQ ID NO: 52), respectively.

Figure 9:
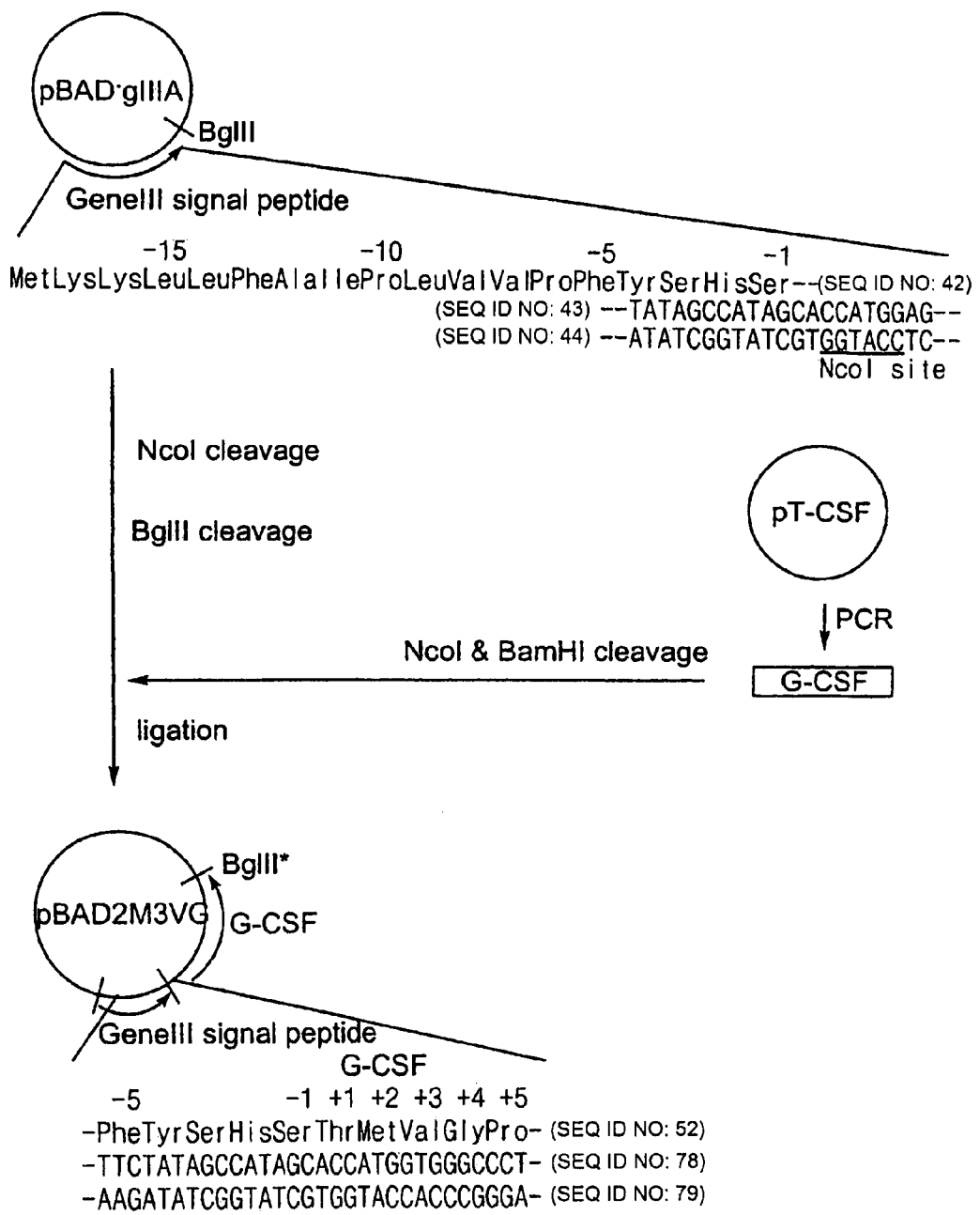
FIG. 9: the procedure for constructing vector pBAD2M3VG.

FIG. 9 shows the above procedure for constructing vector pBAD2M3VG.

E. coli BL21(DE3) (Stratagene, USA) was transformed with vector pBAD2M3VG to obtain a transformant designated E. coli HM 10510, which was deposited with Korean Culture Center of Microorganisms (KCCM) on Mar. 24, 1999 under accession number of KCCM-10153.

(c) Production of [Ser17] hG-CSF

Vector pBADG obtained in (a) was subjected to PCR using a sense primer (SEQ ID NO: 32) designed to substitute Ser codon for the 17th codon of hG-CSF and a complementary antisense primer (SEQ ID NO: 33) in accordance with the procedure of Step 4 of Example 2 to obtain a modified plasmid.

E. coli XL-1 blue (Novagen, USA) was transformed with the modified plasmid. The base sequence of the DNA recovered from transformed colonies was determined, and thus obtained was plasmid pBAD17SG which contained a gene having Ser in place of the 17th amino acid of hG-CSF.

E. coli BL21(DE3) (Stratagene, USA) was transformed with vector pBAD17SG to obtain a transformant designated E. coli HM 10511.

(d) Production of [Met2, Val3, Ser17] hG-CSF

Vector pBAD2M3VG obtained in (b) was subjected to PCR using a sense primer (SEQ ID NO: 32) designed to substitute Ser codon for the 17th codon of hG-CSF and a complementary antisense primer (SEQ ID NO: 33) in accordance with the procedure of Step 4 of Example 2 to obtain a modified plasmid.

E. coli XL-1 blue (Novagen, USA) was transformed with the modified plasmid. The base sequence of the DNA recovered from transformed colonies was determined, and thus obtained was plasmid pBAD2M3V17SG which contained a gene having Met, Val and Ser in place of the 2nd, 3rd and 17th amino acids of hG-CSF, respectively.

E. coli BL21(DE3) (Stratagene, USA) was transformed with vector pBAD2M3V17SG to obtain a transformant designated E. coli HM 10512.

EXAMPLE 8

Production of hG-CSF

Transformants prepared in Examples 2 to 7 were cultured in LB medium (1% bacto-tryptone, 0.5% bacto-yeast extract and 1% NaCl) and then incubated in the presence of an expression inducer (IPTG) for 3 hours or cultured in the absence of IPTG more than 15 hours. Each of the cultures was centrifuged at 6,000 rpm for 20 min. to precipitate bacterial cells, and the precipitate was suspended in a 1/10 volume of isotonic solution (20% sucrose, 10 mM Tris-Cl buffer solution containing 1 mM EDTA, pH 7.0). The suspension was allowed to stand at room temperature for 30 min, and then centrifuged at 7,000 rpm for 10 min. to collect bacterial cells. The cells were resuspended in D.W. at 4° C. and centrifuged at 7,000 rpm for 10 min. to obtain a supernatant as a periplasmic solution. The hG-CSF level in the periplasmic solution was assayed in accordance with ELISA method (Kato, K. et al., *J. Immunol.*, 116, 1554 (1976)) using an antibody against hG-CSF (Aland, USA), which was calculated as the amount of hG-CSF produced per 1 l of culture. The results are shown in Table I.

TABLE 1

| Transformant | Example | Expression Vector | hG-CSF Level in periplasm(mg/l) |
|---|---|---|---|
| HM 10301 | 2(Step 4) | pT14SSG | 65 |
| HM 10302 | 2(Step 7) | pT140SSG-4T22Q | 277 |
| HM 10310 | 2(Step 3) | pT14SS1SG | 92 |
| HM 10311 | 3 | pT14SS1S17SEG | 1,512 |
| HM 10401 | 5 | pTOG | 85 |
| HM 10409 | 4 | pTO1SG | 105 |
| HM 10410 | 6(a) | pTO1S17SG | 1,477 |
| HM 10411 | 6(b) | pTO17SG | 1,550 |
| HM 10413 | 6(c) | pTO17TG | 1,373 |
| HM 10414 | 6(d) | pTO17AG | 1,486 |
| HM 10415 | 6(e) | pTO17GG | 1,480 |
| HM 10416 | 6(f) | pTO17APG | 67 |
| HM 10501 | 7(a) | pBADG | 54 |
| HM 10510 | 7(b) | pBAD2M3VG | 69 |
| HM 10511 | 7(c) | pBAD17SG | 937 |
| HM 10512 | 7(d) | pBAD2M3V17SG | 983 |

EXAMPLE 9

Purification of hG-CSF

Transformant *E. coli* HM 10411 prepared in Example 6(b) was cultured in LB medium and the culture was centrifuged for 6,000 rpm for 20 min. to harvest cells. The periplasmic solution was prepared from the cells by repeating the procedure of Example 8.

The periplasmic solution was adjusted to pH 5.0 to 5.5, adsorbed on a CM-Sepharose (Pharmacia Inc., Sweden) column pre-equilibrated to pH 5.3, and then, the column was washed with 25 mM NaCl. hG-CSF was eluted by sequentially adding to the column buffer solutions containing 50 mM, 100 mM and 200 mM NaCl, and fractions containing hG-SCF were collected and combined.

The combined fractions were subjected to Phenyl Sepharose (Pharmacia Inc., Sweden) column chromatography to obtain [Ser17] hG-CSF having a purity of 99%.

Further, the above procedure was repeated using each of the transformants *E. coli* HM 10311, HM 10409, HM 10411, HM 10413, HM 10414, HM 10415, HM 10510 and HM 10512 prepared in Examples 3, 4, 6(b), 6(c), 6(d), 6(e), 7(b) and 7(d), respectively.

Each of the purified hG-CSF fraction was subjected to sodium dodecylsulfate polyacrylamide gel electrophoresis (SDS-PAGE) to determine the purity and approximate concentration of the hG-CSF, and then subjected to ELISA to determine the exact hG-CSF concentration in the periplasmic solution. Met-hG-CSF (Kirin amgen) was used as a control.

Figure 10A:
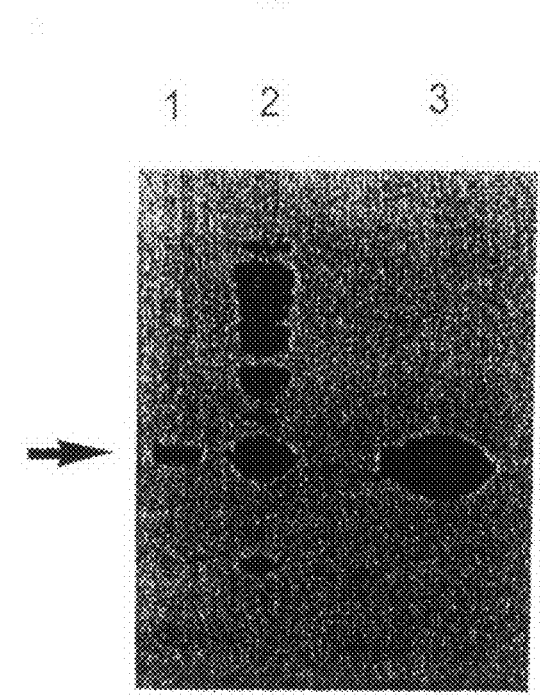
FIGS. 10a and 10b: the results of western blot analyses which verily the expression of hG-CSF and modified hG-CSFs from recombinant cell lines and the molecular weight of expressed proteins, respectively.

FIG. 10a reproduces the SDS-PAGE result, wherein lane 1 shows Met-G-CSF, lane 2, the periplasmic solution of the transformant *E. coli* HM 10411, and lane 3, the purified [Ser17] hG-CSF. As can be seen from FIG. 10b, the molecular weight of [Ser17] hG-CSF is the same as that of wild-type hG-CSF and the periplasmic solution of the transformant *E. coli* HM 10411 contains a high level of [Ser17] hG-CSF.

Further, the N-terminal amino acid sequences of hG-CSFs were determined and the nucleotide sequences coding for the 1st to 32nd amino acids produced using the transformants HM 10311, HM 10409, HM 10411, HM 10413, HM 10414, HM 10415, HM 10510 and HM 10512 shown in SEQ ID NOS: 56, 58, 60, 62, 64, 66, 68 and 70, respectively. The result shows that the modified hG-CSF produced according to the present invention is not methionylated at N-terminus.

Figure 10B:
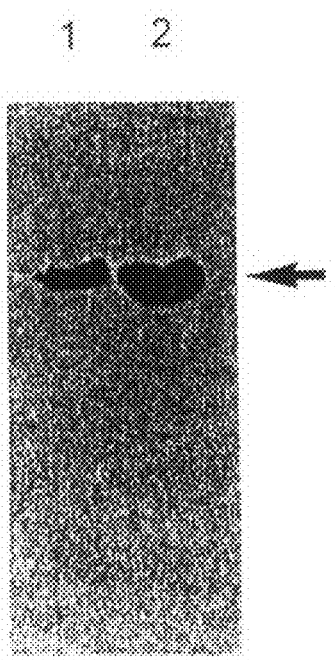

A nitrocellulose filter (Bio-Rad Lab, USA) was wetted with a buffer solution for blotting (170 mM glicine, 25 mM Tris.HCl (PH 8), 20% methanol) and the proteins separated on the gel were western blotted onto a nitrocellulose filter (Bio-Rad Lab., USA.) for 3 hours. The filter was kept in 1% Casein for 1 hour and was washed three times with PBS containing 0.05% Tween 20. The filter was put in a goat anti-G-CSF antibody (R&D System, AB-214-NA, USA) solution diluted with PBS and reacted at room temperature for 2 hours. After reaction, the filter was washed 3 times with a PBST solution to remove unreacted antibody. Horseradish peroxidase-conjugated rabbit anti-goat IgG (Bio-Rad Lab., USA) diluted with PBS was added thereto and reacted at room temperature for 2 hour. The filter was washed with PBST, and a peroxidase substance kit (Bio-Rad Lab., USA) solution was added thereto to develop a color reaction. The results from the above western blotting are shown in FIG. 10b, wherein lane 1 represents a positive control, Met-G-CSF, and lane 2, purified [Ser17] hG-CSF. As can be seen from FIG. 10b, the molecular weight of [Ser17] hG-CSF equals that of wild-type hG-CSF.

EXAMPLE 10

Cellular Activity of hG-CSF and Modified hG-CSF

Cell line HL-60 (ATCC CCL-240 derived from the bone marrow of a promyelocytic leukemia patient/a white 36-year-old woman) was cultured in RPMI 1640 media containing 10% fetal bovine serum and adjusted to $2.2 \times 10^5$ cells/ml, followed by adding thereto DMSO (dimethylsulfoxide, culture grade/SIGMA) to a concentration of 1.25% (v/v). 90 μl of the resulting solution was added to a 96 well plate (Corning/low evaporation 96 well plate) in an amount of $2 \times 10^4$ cells/well and incubated at 37° C. under 5% CO2 for 48 hours.

Each of the modified [Ala17] hG-CSF, [Gly 17] hG-CSF, [Ser17] hG-CSF, and [Thr 17] hG-CSF was diluted in RPMI 1640 media to a concentration of 500 ng/ml and then serially diluted 10 times by 2-fold with RPMI 1640 media.

The resulting solution was added to wells at 10 μl per well and incubated at 37° C. for 48 hours. As a positive control, a commercially available hG-CSF (Jeil Pharmaceutical.).

The level of cell line increased was determined using a commercially available CellTiter96™ (Cat # G4100, Promega) based on the measured optical density at 670 nm.

Figure 11:
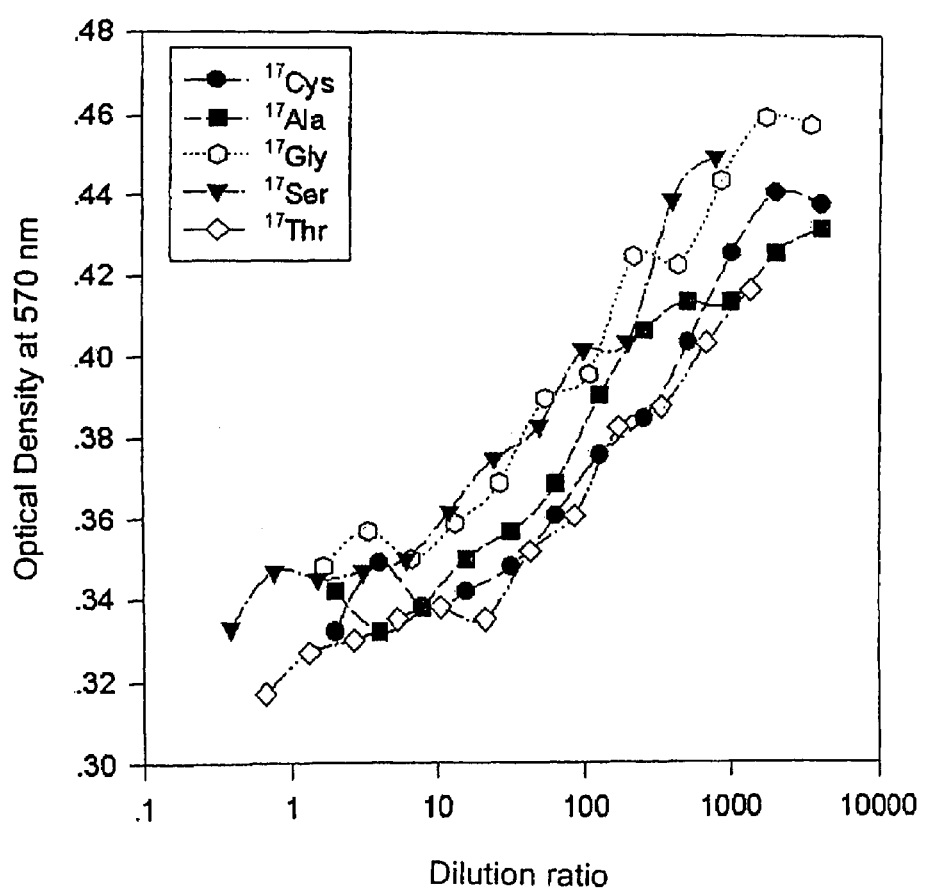
FIG. 11: the cellular activities of hG-CSF and modified hG-CSF produced from recombinant cell lines.

As can be seen from FIG. 11, the cellular activities of the modified hG-CSFs are the same as, or higher than of that the positive control, wild-type hG-CSF.

While the embodiments of the subject invention have been described and illustrated, it is obvious that various changes and modifications can be made therein without departing from the spirit of the present invention which should be limited only by the scope of the appended claims.

What is claimed is:

1. A modified human granulocyte-colony stimulating factor(hG-CSF) which is different from a parent wild-type hG-CSF of the amino acid sequence of SEQ ID NO: 2 by having at least one replacements of amino acid residues at the positions 1st, 2nd, 3rd and 17th amino acids of the wild-type hG-CSF, wherein the replaced amino acids in the modified hG-CSF are different from one present in the parent wild-type hG-CSF;

wherein the modified hG-CSF has no sugar chain;

wherein the modified hG-CSF has no terminal Met residue at the N-terminus thereof;

wherein when the 1st amino acid is replaced, the first amino acid in the modified hG-CSF is Ser; and when the 17th amino acid is replaced, the 17th amino acid in the modified hG-CSF is an amino acid which is not charged at neutral pH.

2. The modified hG-CSF of claim 1 having an amino acid sequence which is the same as that of the parent wild-type hG-CSF, except that (a) the 1st amino acid is Ser;
(b) the 1st amino acid is Ser and the 17th amino acid is X;
(c) the 2nd amino acid is Met and the 3rd amino acid is Val;
(d) the 2nd amino acid is Met, the 3rd amino acid is Val and the 17th amino acid is X; or
(f) the 17th amino acid is X, wherein X is an amino acid which is not charged at neutral pH.

3. The modified hG-CSF of claim 2, wherein X is selected from the group consisting of Ser, Thr, Ala and Gly.

4. The modified hG-CSF of claim 3, wherein X is Ser.

5. A DNA encoding the modified hG-CSF of claim 1.

6. The DNA of claim 5, wherein the 1st to the 60th nucleotide sequence of the modified hG-CSF DNA corresponds to one selected from the group consisting of SEQ ID NOS: 55, 57, 59, 61, 63, 65, 67 and 69.

7. An expression vector comprising the DNA of claim 5.

8. The expression vector of claim 7, which further comprises a polynucleotide encoding a signal peptide attached at the 5'-end of the DNA encoding the modified hG-CSF.

9. The expression vector of claim 8, wherein the signal peptide is an E.coli thermoresistant enterotoxin II signal peptide or a modified E.coli thermoresistant enterotoxin II signal peptide.

10. The expression vector of claim 9, wherein the E.coli thermoresistant enterotoxin II signal peptide has the amino acid sequence of SEQ ID NO: 53.

11. The expression vector of claim 7, which is pT14SS1SG, pT14SS1S17SEG, pTO1SG, pTO1S17SG, pTO17SG or pBAD2M3V17SG.

12. A microorganism transformed with the expression vector according to claim 7.

13. The microorganism of claim 12, which is a transformed E.coli.

14. The microorganism of claim 13, wherein the transformed E.coli is selected from the group consisting of E. coli BL21(DE3)/pT14SS1SG(HM 10310), E. coli BL21(DE3)/pT14SS1S17SEG(HM 10311, KCCM-10154), E. coli BL21(DE3)/pTO1SG(HM 10409), E. coli BL21(DE3)/pTO1S17SG(HM 10410, KCCM-10151), E. coli BL21(DE3)/pTO17SG(HM 10411, KCCM-10152), E.coli BL21(DE3)/pTO17TG(HM 10413), E. coli BL21(DE3)/pTO17AG(HM 10414), E. coli BL21(DE3)/pTO17GG(HM 10415), E. coli BL21(DE3)/pBAD2M3VG(HM 10510, KCCM-10153), E. coli BL21(DE3)/pBAD17SG(HM 10511) or E. coli BL21(DE3)/pBAD2M3V17SG(HM 10512).

15. A process for producing a modified hG-CSF in microorganism which comprises culturing the transformed microorganism of claim 12 to produce and secrete the modified hG-CSF to a periplasm.

16. A DNA encoding the modified hG-CSF of claim 2.

17. A DNA encoding the modified hG-CSF of claim 3.

18. A DNA encoding the modified hG-CSF of claim 4.

19. The expression vector of claim 8, which is pT14SS1SG, pT14SS1S17SEG, pTO1SG, pTO1S17SG, pTO17SG or pBAD2M3V17SG.

20. A microorganism transformed with the expression vector according to claim 8.

21. The DNA of claim 6, wherein the 1st to the 60th nucleotide sequence of the modified hG-CSF DNA corresponds to SEQ ID NO: 59.

22. The modified hG-CSF of claim 1, which has an amino acid sequence of SEQ ID NO: 60.

23. The expression vector of claim 9, wherein the modified E.coli thermoresistant enterotoxin II signal peptide has the amino acid sequence of SEQ ID NO: 54.

24. The expression vector of claim 9, which further comprises a modified E coli beta enterotoxin II Shine-Dalgano sequence having the amino acid sequence of SEQ ID NO: 71.

25. The expression vector of claim 8, wherein the signal peptide is E.coli beta lactamase signal peptide or modified E.coli beta lactamase signal peptide.

26. The expression vector of claim 25, wherein the E.coli beta lactamase signal peptide has the amino acid sequence of SEQ ID NO: 24.

27. The expression vector of claim 8, wherein the signal peptide is bacteriophage fd Gene III signal peptide.

28. The expression vector of claim 27, wherein the bacteriophage fd Gene III signal peptide has the amino acid sequence of SEQ ID NO: 42.

* * * * *